US009611471B2

(12) United States Patent
van Roon-Mom et al.

(10) Patent No.: US 9,611,471 B2
(45) Date of Patent: Apr. 4, 2017

(54) ANTISENSE OLIGONUCLEOTIDE DIRECTED REMOVAL OF PROTEOLYTIC CLEAVAGE SITES FROM PROTEINS

(75) Inventors: Wilhelmina M. C. van Roon-Mom, Beverwijk (NL); Melvin Maurice Evers, Utrecht (NL); Barry Antonius Pepers, Leiden (NL); Annemieke Aartsma-Rus, Hoofddorp (NL); Garrit-Jan Boudewijn Van Ommen, Amsterdam (NL)

(73) Assignee: Academisch Ziekenhuis Leiden, Leiden (NL)

( * ) Notice: Subject to any disclaimer, the term of this patent is extended or adjusted under 35 U.S.C. 154(b) by 367 days.

(21) Appl. No.: 13/814,203

(22) PCT Filed: Aug. 4, 2011

(86) PCT No.: PCT/NL2011/050549
§ 371 (c)(1), (2), (4) Date: Apr. 12, 2013

(87) PCT Pub. No.: WO2012/018257
PCT Pub. Date: Feb. 9, 2012

(65) Prior Publication Data

US 2013/0198877 A1 Aug. 1, 2013

Related U.S. Application Data

(60) Provisional application No. 61/370,855, filed on Aug. 5, 2010.

(30) Foreign Application Priority Data

Aug. 5, 2010 (EP) .................................... 10172076

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/11* (2013.01); *C12N 2320/33* (2013.01)

(58) Field of Classification Search
CPC .............. C12N 15/113; C12N 2310/11; C12N 2310/346; C12N 2320/33; C12N 2320/34
USPC ................................. 514/44; 536/23.1, 24.5
See application file for complete search history.

(56) References Cited

U.S. PATENT DOCUMENTS

2002/0049173 A1* 4/2002 Bennett ............. C12N 15/1135 514/44 A
2003/0235845 A1 12/2003 van Ommen et al.
2006/0099616 A1 5/2006 van Ommen et al.
2006/0147952 A1 7/2006 van Ommen et al.
2006/0172962 A1* 8/2006 Vickers ................ C12N 15/113 514/44 A
2007/0299027 A1 12/2007 Hung et al.
2008/0039418 A1 2/2008 Freier
2008/0200409 A1 8/2008 Wilson et al.
2008/0209581 A1 8/2008 van Ommen et al.
2009/0011004 A1* 1/2009 Lutz et al. .................... 424/450
2009/0076246 A1 3/2009 van Deutekom
2009/0228998 A1 9/2009 van Ommen et al.
2010/0069472 A1 3/2010 Hung et al.
2010/0184833 A1 7/2010 De Kimpe et al.
2012/0270930 A1 10/2012 Van Der Maarel et al.

FOREIGN PATENT DOCUMENTS

WO 0224906 A1 3/2002
WO 2004083432 A1 9/2004
WO 2004083446 A2 9/2004
WO 2007089584 A2 8/2007
WO 2007089611 A2 8/2007
WO 2008018795 A1 2/2008
WO WO 2008/018795 * 2/2008
WO 2012018257 A1 2/2012

OTHER PUBLICATIONS

Chelly et al, Nature 344(6261):64-65, 1990; abstract only.*
GenBank NM_002111.7, Mar. 2015.*
McClorey et al, Gene Therapy 13:1373-1381, 2006.*
Gafni et al, J. Biol. Chem. 279(19): 20211-20220, 2004.*
Graham et al, Cell 125:1179-1191, 2006.*
Wilton et al, Mol. Therapy 15(7):1288-1296, 2007.*
Karras et al, Mol. Pharmacol. 58:380-387, 2000.*
ExPASy Peptide Cutter, IL-5R sequence analysis created Sep. 19, 2016.*
PROSPER, IL-5R sequence analysis created Sep. 21, 2016.*
Gregory et al, J. Immunol. 170:5359-5366, 2003.*
ExPASy Peptide Cutter, Bcl-x sequence analysis created Sep. 19, 2016.*
PROSPER, Bcl-x sequence analysis created Sep. 21, 2016.*
Boise et al, Cell 74(4):597-608, 1993.*
Nijhawan et al, Ann. Rev. Neurosci. 23:73-87, 2000.*
Sumantran et al, Cancer Res. 55: 2507-2510, 1995.*
Owens, Current Topics in Micrbiol. & Immunol. 336:105-120, in Toll-like Receptors: Roles in Infection and Neuropathology, T. Kielian (ed.), Springer-Verlag Berlin Heidelberg, 2009.*
Wilton et al., Antisense Oligonucleotide-induced Exon Skipping Across the Human Dystrophin Gene Transcript, Molecular Therapy, Jul. 2007, pp. 1288-1296, vol. 15, No. 7.
Spitali et al., Exon Skipping-Mediated Dystrophin Reading Frame Restoration for Small Mutations, Human Mutation, Nov. 2009, pp. 1527-1534, vol. 30, No. 11.
Mehler, Mark F., Brain dystrophin, neurogenetics and metal retardation, Brain Research Reviews, Apr. 2000, pp. 277-307, vol. 32, No. 1.
Database Biosis (Online) Biosciences Information Service, Philadelphia, PA, US, 2009, Oligonucleotide Therapeutics.

(Continued)

*Primary Examiner* — Kevin Hill
(74) *Attorney, Agent, or Firm* — TraskBritt P.C.

(57) ABSTRACT

Described are means and methods for removing a proteolytic cleavage site from a protein, the method comprising providing a cell that expresses pre-mRNA encoding the protein with an anti-sense oligonucleotide that induces skipping of the exonic sequence that encodes the proteolytic cleavage site, and allowing translation of mRNA produced from the pre-mRNA.

6 Claims, 6 Drawing Sheets

(56) References Cited

OTHER PUBLICATIONS

Mineur et al., Newly identified biologically active and proteolysis-resistant VEGF-A isoform VEGF111 is induced by genotoxic agents, Journal of Cell Biology, Dec. 17, 2007, pp. 1261-1273, vol. 179, No. 6.

Kurreck, Jens, Antisense technologies, Improvement through novel chemical modifications, Eur. J. Biochem., 2003, pp. 1628-1644, vol. 270.

Ichikawa et al., The genomic structure and expression of MJD, the Machado-Joseph disease gene, J. Hum. Genet. 2001, pp. 413-422, vol. 46.

Hu et al., Inhibiting Expression of Mutant Huntingtin and Ataxin-3 by Targeting Expanded CAG Repeat RNAs, Nature Biotechnol., May 2009, pp. 478-484, vol. 27, No. 5.

Mulders et al., Triplet-repeat oligonucleotide-mediated reversal of RNA toxicity in myotonic dystrophy, RNAS, 2009, pp. 13915-13920, vol. 106, No. 33.

Livingston et al., GenBank Accession EU009923, 2007.

* cited by examiner 9 10 11 12 13 14

9 10 11 12 13 14

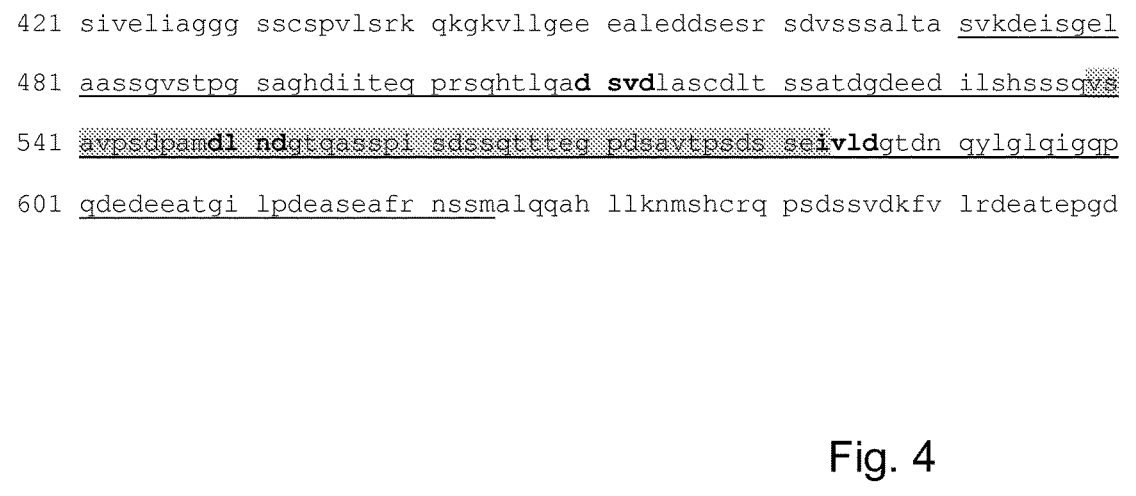

421 siveliaggg sscspvlsrk qkgkvllgee ealeddsesr sdvsssalta svkdeisgel 481 aassgvstpg saghdiiteq prsqhtlqad svdlascdlt ssatdgdeed ilshsssqvs 541 avpsdpamdl ndgtqasspi sdssgttteg pdsavtpsds seivldgtdn qylglqigqp 601 qdedeeatgi lpdeaseafr nssmalqqah llknmshcrq psdssvdkfv lrdeatepgd

Fig. 4

| | | | | | | | | | | | | | | | | | | | | | | | | | |
|---|---|---|---|---|---|---|---|---|---|---|---|---|---|---|---|---|---|---|---|---|---|---|---|---|---|
| TCC | AGC | CAG | GTC | AGC | GCC | GTC | CCA | TCT | GAC | CCT | GCC | ATG | **GAC** | **CTG** | **AAT** | **GAT** | GGG | ACC | CAG | GCC | TCG | TCG | CCC | ATC | AGC | Nucleotide |
| S | S | Q | V | S | A | V | P | S | D | P | A | M | D | L | N | D | G | T | Q | A | S | S | P | I | S | Amino Acid |

| | | | | | | | | | | | | | | | | | | | | | | | | |
|---|---|---|---|---|---|---|---|---|---|---|---|---|---|---|---|---|---|---|---|---|---|---|---|---|
| GAC | AGC | TCC | CAG | ACC | ACC | ACC | GAA | GGG | CCT | GAT | TCA | GCT | GTT | ACC | CCT | TCA | GAC | AGT | TCT | GAA | **ATT** | **GTG** | **TTA** | **GAC** | GGT | Nucleotide |
| D | S | S | Q | T | T | T | E | G | P | D | S | A | V | T | P | S | D | S | S | E | I | V | L | D | G | Amino Acid |

Exon 12 | Exon 13

ANTISENSE OLIGONUCLEOTIDE DIRECTED REMOVAL OF PROTEOLYTIC CLEAVAGE SITES FROM PROTEINS

CROSS-REFERENCE TO RELATED APPLICATIONS

This application is a national phase entry under 35 U.S.C. §371 of International Patent Application PCT/NL2011/050549, filed Aug. 4, 2011, designating the United States of America and published in English as International Patent Publication WO 2012/018257 A1 on Feb. 9, 2012, which claims the benefit under Article 8 of the Patent Cooperation Treaty and under 35 U.S.C. §119(e) to U.S. Provisional Patent Application Ser. No. 61/370,855, filed Aug. 5, 2010, and to European Patent Application Serial No. 10172076.1, filed Aug. 5, 2010.

STATEMENT ACCORDING TO 37 C.F.R. §1.821(C) OR (E)—SEQUENCE LISTING SUBMITTED AS A TXT AND PDF FILES

Pursuant to 37 C.F.R. §1.821(c) or (e), files containing a TXT version and a PDF version of the Sequence Listing have been submitted concomitant with this application, the contents of which are hereby incorporated by reference.

TECHNICAL FIELD

The disclosure relates to the field of biotechnology and genetic and acquired diseases. The disclosure, in particular, relates to the alteration of mRNA processing of specific pre-mRNA to remove a proteolytic cleavage site from a protein encoded by the pre-mRNA.

BACKGROUND

Proteolytic processing is a major form of post-translational modification that occurs when a protease cleaves one or more bonds in a target protein to modify its activity. This processing may lead to activation, inhibition, alteration or destruction of the protein's activity. Many cellular processes are controlled by proteolytic processing. The attacking protease may remove a peptide segment from either end of the target protein, but it may also cleave internal bonds in the protein that lead to major changes in the structure and function of the protein.

Proteolytic processing is a highly specific process. The mechanism of proteolytic processing varies according to the protein being processed, location of the protein, and the protease.

Proteolytic processing can have various functions. For instance, proteolysis of precursor proteins regulates many cellular processes including gene expression, embryogenesis, the cell cycle, programmed cell death, intracellular protein targeting and endocrine/neural functions. In all of these processes, proteolytic cleavage of precursor proteins is necessary. The proteolysis is often done by serine proteases in the secretory pathways. These proteases are calcium-dependent serine endoproteases and are related to yeast and subtilisin proteases and, therefore, called Subtilisin-like Proprotein Convertases (SPCs) or PCs. Seven members of this family have been identified and characterized and each have conserved signal peptides, pro-regions, catalytic and P-domains but differ in their C-terminal domains in mammals.

Autocatalytic cleavage of an N-terminal propeptide activates these proteases, which is required for folding, and activity also causes the release of prodomain. Other examples of function associated with proteolytic processing are the blood clotting cascades, the metaloendopeptidases, the secretases and the caspases. Yet other examples are the viral proteases that specifically process viral polyproteins.

The art describes various strategies to inhibit the various proteases. For instance, gamma-secretase inhibitors are presently being developed for the treatment of T cell acute lymphoblastic leukemia (*Nature Medicine* 2009, 15:50-58). Caspase inhibitors are being developed for a variety of different applications (*The Journal of Biological Chemistry* 1998, 273:32608-32613), for instance, in the treatment of sepsis (*Nature Immunology* 2000, 1:496-501).

A problem with the use of protease inhibitors is that these proteins typically have a range of targets in the human body and, associated therewith, a range of effects. Inhibiting a protease in the human body through the action of a protease inhibitor thus, not only inhibits the desired effect, but typically also has a range of other effects that may or may not affect the utility of the protease inhibitor for the indicated disease. Another problem associated with protease inhibitors is that it is not always easy to produce an inhibitor that is sufficiently specific for the target protease and, therefore, may also inhibit other proteases.

DISCLOSURE

The disclosure provides an alternative approach to interfere with the proteolytic processing of target proteins. Instead of designing inhibitors to the proteases, the target protein itself is modified. In the art, it is known to modify a protease cleavage site in a target protein. This is typically done by introducing point mutations into the coding region of a protein. These mutations typically break up the recognition sequence of the protease. These types of modification are usually introduced into a cDNA copy of the gene and this altered copy is inserted into the DNA of cells by recombinant DNA technology. Although this can be done in the laboratory, it is difficult to implement such strategies in the clinic, if only because gene therapy applications that rely on the introduction of a complete gene are, at present, not very efficient, and the original gene associated with the problem is not removed.

The disclosure provides a method for removing a proteolytic cleavage site from a protein comprising providing a cell that expresses a pre-mRNA encoding the protein with an antisense oligonucleotide (AON) that induces skipping of the exon sequence that encodes the proteolytic cleavage site, the method further comprising allowing translation of mRNA produced from the pre-mRNA. A method hereof is particularly useful for removing proteolytic cleavage sites from proteins. It does not require removal or modification of the gene itself, but rather, prevents the incorporation of the genetic code for the proteolytic cleavage site into the coding region of the protein in the mature mRNA. In this way, the process is reversible. The oligonucleotide has a finite life span in the cell and, therefore, has a finite effect on the removal. Another advantage is that the removal is not absolute. Not all pre-mRNA coding for the target protein that is generated by the cell is typically targeted. It is possible to achieve high levels of skipping. The skipping efficiency depends, for instance, on the particular target, the particular exon sequence to be skipped, the particular AON design, and/or the amount of AON used. Skipping percentages are typically expressed as the ratio of mRNA that does not have the coding part of the proteolytic cleavage site (skipped mRNA) versus the sum of skipped mRNA and unmodified mRNA coding for the unmodified target protein (unmodified mRNA). The possibility of tailoring the percentage of skipping is advantageous; for instance, when the unmodified protein is associated with a toxic phenotype but also has a positive function to perform that is not performed (as well) by the modified protein. By removing the proteolytic cleavage site only from a fraction of the protein formed, it is possible to reduce the toxic property, while leaving the positive or desired function of the unmodified protein at least partially intact.

The invention modulates the splicing of a pre-mRNA into an mRNA, such that an exon sequence that codes for a proteolytic cleavage site that is present in the exons encoded by the pre-mRNA is not included in the mature mRNA produced from the pre-mRNA. Protein that is subsequently translated from this mRNA does not contain the proteolytic cleavage site. The invention, thus, does not actually remove a proteolytic cleavage site from a protein that has already been formed. Rather, it promotes the production of a novel protein that does not contain the proteolytic cleavage site. However, when looking at a cell as an entity wherein protein synthesis and degradation are at equilibrium, the result of a method of the invention can be seen as removing a proteolytic cleavage site from a protein. Unmodified target protein is gradually replaced by target protein that does not contain the proteolytic cleavage site. Thus, provided is a method for producing a cell that contains a modified protein that lacks a proteolytic cleavage site, when compared to the unmodified protein encoded in the genome, the method comprising providing a cell that expresses pre-mRNA encoding the protein with an AON that induces skipping of the exon sequence or part of the exon sequence that encodes the proteolytic cleavage site, the method further comprising allowing translation of mRNA produced from the pre-mRNA in the cell. The novel mRNA from which the coding sequence for the proteolytic cleavage site is removed is a shortened or smaller coding sequence that codes for a shorter or smaller version of the unmodified protein. Often, the modified protein is an internally deleted version of the unmodified protein, wherein the internal deletion at least breaks up and, preferably, deletes the proteolytic cleavage site.

Antisense-mediated modulation of splicing (also referred to as exon-skipping) is one of the fields where AONs have been able to live up to their expectations. In this approach, AONs are implemented to facilitate cryptic splicing, to change levels of alternatively spliced genes, or, in case of Duchenne muscular dystrophy (DMD), to skip an exon in order to restore a disrupted reading frame. The latter allows the generation of internally deleted, but largely functional, dystrophin proteins and would convert a severe DMD into a milder Becker muscular dystrophy phenotype. In fact, exon skipping is currently one of the most promising therapeutic tools for DMD, and a successful first-in-man trial has recently been completed. The antisense-mediated modulation of splicing has been diversified since its first introduction and now many different kinds of manipulations are possible. Apart from classical exon skipping where typically an entire exon is skipped from the mature mRNA, it is, for instance, possible to skip a part of an exon. Exon inclusion is also possible. The latter occurs when AONs targeted toward appropriate intron sequences are coupled to the business end of SR-proteins.

Exon skipping has been used to restore cryptic splicing, to change levels of alternatively spliced genes, and to restore disrupted open reading frames. This approach has been employed with a number of genes including Apolipoprotein B, Bcl-X, Collagen type 7, dystrophin, dysferlin, prostate-specific membrane antigen, IL-5 receptor alpha, MyD88, Tau, TNFalpha2 receptor, Titin, WT1, beta-globulin, and CFTR. Accordingly, in preferred embodiments, methods are provided for removing a proteolytic cleavage site from a protein, wherein the protein is not Apolipoprotein B, Bcl-X, Collagen type 7, dystrophin, dysferlin, prostate-specific membrane antigen, IL-5 receptor alpha, MyD88, Tau, TNFalpha2 receptor, Titin, WT1, beta-globulin, or CFTR; more preferably, the protein is not dystrophin.

In contrast to the previous uses for exon-skipping, provided is a method for removing a proteolytic cleavage site in order to treat an individual, restore function to a protein, or reduce toxicity of a protein. The methods and oligonucleotides described herein are particularly useful for removing proteolytic cleavage sites from a protein, wherein the protein is involved in a neurodegenerative disorder.

Prevention of inclusion of a coding part for a proteolytic cleavage site into mature mRNA is, in the present invention, typically achieved by means of exon-skipping. Antisense oligonucleotides for exon-skipping typically enable skipping of an exon or the 5' or 3' part of it. Antisense oligonucleotides can be directed toward the 5' splice site, the 3' splice site, to both splice sites, to one or more exon-internal sites and to intron sequences, for instance, specific for the branch point. The latter enables skipping of the upstream exon.

Skipping of the nucleotides that code for the proteolytic cleavage site is typically achieved by skipping the exon that contains the nucleotides that code for the proteolytic cleavage site. The proteolytic cleavage site comprises the recognition sequence for the specific protease and the two amino acids between which the peptide linkage is cleaved by the protease. The proteolytic cleavage site can overlap the boundary of two adjacent exons or, if a part of the exon is skipped, overlap the exon sequence that contains the cryptic splice acceptor/donor sequence. In this embodiment, it is preferred to skip the exon sequence that codes for the peptide linkage that is cleaved by the protease. Whether or not a recognition sequence for a protease is actually used in nature depends, not only on the presence of the recognition sequence itself, but also on the location of the site in the folded protein. An internally located recognition site is typically not used in nature. In the invention, a proteolytic cleavage site is an active proteolytic cleavage site that is actually used in nature.

Skipping of the exon that contains the nucleotides that code for the proteolytic cleavage site is preferably achieved by means of an AON that is directed toward an exon internal sequence. An oligonucleotide is said to be directed toward an exon internal sequence if the complementarity region that contains the sequence identity to the reverse complement of the target pre-mRNA is within the exon boundary. Presently, all exons that have been targeted by means of exon-skipping can be induced to be skipped from the mature mRNA, often with one AON and sometimes with two AONs directed toward the exon. However, not all AONs that can be designed induce detectable amounts of skipping. The most experience with exon-skipping has been gained in the DMD system. Using AON directed toward exon-internal sequences, it has been shown that all exons can be skipped (with the exception, of course, of the first and the last exon). However, not all AON designed against an exon-internal sequence actually induce detectable amounts of skipping of the targeted exon. The frequency of randomly selected exon-internal AON that induce skipping is around 30%, depending on the actual exon that is targeted. Since the first trials, however, the experience gained from AON that successfully induced skipping has resulted in a significant improvement of the success ratio of a designed AON (PMID: 18813282, Aartsma-Rus et al., *Mol. Ther.* 17(3):548 (2009). The factors that improve the success ratio include, among others, the predicted structure of the exon RNA at the target site, the exact sequence targeted, and the predicted presence or absence of specific SR-protein binding sites in the target site (ibidem).

Skipping of an exon sequence encoding a proteolytic cleavage site is preferably such that downstream amino acids of the target protein are present in the newly formed protein. In this way, the proteolytic cleavage site is removed while leaving much of the downstream protein intact. In this embodiment, the functionality of the modified protein is at least part of the functionality of the protein as present in normal individuals. Thus, preferably, the modified protein contains an “in frame” deletion of the proteolytic cleavage site. Preferably, the “in frame” deleted protein has at least 20%, preferably at least 50% of the functionality of the unmodified protein in a normal individual. Thus, in a preferred embodiment, the number of nucleotides that is skipped is dividable by three. Skipping of an exon sequence that codes for a proteolytic cleavage site is typically achieved by skipping the exon that contains this sequence. Skipping of the target exon is sufficient if this exon contains a number of nucleotides that is dividable by three. If the exon contains another number, it is preferred to also skip an adjacent exon, such that the total number of skipped nucleotides is again dividable by three. In most cases, the skipping of an adjacent exon is sufficient; however, if this also does not result in a number of skipped nucleotides that is dividable by three, the skipping of yet a further exon, adjacent to the two mentioned, may be necessary. Skipping of four or more exons is possible but often does not yield a lot of the correct protein. Sometimes, it is possible to skip only a part of an exon. This is either the 5' part of the 3' part of the exon. This occurs when the exon contains a cryptic 3' or 5' splice site that can be activated.

The term “pre-mRNA” refers to a non-processed or partly processed precursor mRNA that is synthesized from a DNA template in the cell nucleus by transcription. Within the context of the invention, inducing and/or promoting skipping of an exon sequence that codes for a proteolytic cleavage site, as indicated herein, means that at least 1%, 10%, 20%, 30%, 40%, 50%, 60%, 70%, 80%, 90% or more of the mRNA encoding of the targeted protein in a cell will not contain the skipped exon sequence (modified/(modified+unmodified) mRNA). This is preferably assessed by PCR as described in the examples.

An AON hereof that induces skipping of an exon sequence that encodes a proteolytic cleavage site, preferably, comprises a sequence that is complementary to the exon. In some embodiments, the AON induces skipping of an exon in its entirety. In other embodiments, the AON induces skipping of a part of an exon, preferably, the part encodes a proteolytic cleavage site. Preferably, the AON contains a continuous stretch of between 8-50 nucleotides that is complementary to the exon. An AON of the invention preferably comprises a stretch of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides that is complementary to the exon. In a preferred embodiment, the AON contains a continuous stretch of between 12-45 nucleotides that is complementary to the exon. More preferably, a stretch of between 15-41 nucleotides. Depending on the chemical modification introduced into the AON the complementary stretch may be at the smaller side of the range or at the larger side. A preferred antisense oligonucleotide, according to the invention, comprises a T-O alkyl phosphorothioate antisense oligonucleotide, such as 2'-O-methyl modified ribose (RNA), 2'-0-ethyl modified ribose, 2'-O-propyl modified ribose, and/or substituted derivatives of these modifications, such as halogenated derivatives. A most preferred AON, comprises of 2'-0-methyl phosphorothioate ribose. Such AON, typically, do not need to have a very large complementary stretch. Such AON, typically, contain a stretch of between 15-25 complementary nucleotides. As described herein below, another preferred AON of the invention comprises a morpholino backbone. AON comprising such backbones typically contain somewhat larger stretches of complementarity. Such AON, typically, contain a stretch of between 25-40 complementary nucleotides. When in this invention reference is made to the range of nucleotides, this range includes the number(s) mentioned. Thus, by way of example, when reference is made to a stretch of between 8-50, this includes 8 and 50.

An AON hereof that is complementary to a target RNA is capable of hybridizing to the target RNA under stringent conditions. Typically, this means that the reverse complement of the AON is at least 90% and, preferably, at least 95% and, more preferably, at least 98% and, most preferably, at least 100% identical to the nucleotide sequence of the target at the targeted sited. An AON hereof, thus preferably, has two or less mismatches with the reverse complement of the target RNA, preferably, it has one or no mismatches with the reverse complement of the target RNA. In another preferred embodiment, the AON may be specifically designed to have one or more mismatches, preferably, one or two mismatches, e.g., in cases where it is necessary to reduce the affinity when the skipping of the 100% complementary AON is more effective than biologically desired in view of the necessary remaining protein activity. A mismatch is defined herein as a nucleotide or nucleotide analogue that does not have the same base pairing capacity in kind, not necessarily in amount, as the nucleotide it replaces. For instance, the base of uracil that replaces a thymine and vice versa, is not a mismatch. A preferred mismatch comprises an inosine. An inosine nucleotide is capable of pairing with any natural base in an RNA, i.e., capable of pairing with an A, C, G or U in the target RNA.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six-membered ring, and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane. One study comparing several of these methods, found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium. A modified backbone is typically preferred to increase nuclease resistance of the AON, the target RNA or the AON/target RNA hybrid, or a combination thereof. A modified backbone can also be preferred because of its altered affinity for the target sequence compared to an unmodified backbone. An unmodified backbone can be RNA or DNA preferably it is an RNA backbone.

It is further preferred that the linkage between the residues in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent, comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of 7V-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) *Chem. Commun,* 495-497). Since the backbone of a PNA molecule contains no charged phosphate groups, PNA-RNA hybrids are usually more stable than RNA-RNA or RNA-DNA hybrids, respectively, (Egholm et al (1993) *Nature* 365, 566-568).

A further preferred backbone, comprises a morpholino nucleotide analog or equivalent, in which the ribose or deoxyribose sugar is replaced by a six-membered morpholino ring. A most preferred nucleotide analog or equivalent, comprises a phosphorodiamidate morpholino oligomer (PMO), in which the ribose or deoxyribose sugar is replaced by a six-membered morpholino ring, and the anionic phosphodiester linkage between adjacent morpholino rings is replaced by a non-ionic phosphorodiamidate linkage.

In yet a further embodiment, a nucleotide analogue or equivalent of the invention, comprises a substitution of one of the non-bridging oxygens in the phosphodiester linkage. This modification slightly destabilizes base-pairing but adds significant resistance to nuclease degradation. A preferred nucleotide analogue or equivalent, comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention, comprises one or more sugar moieties that are mono- or disubstituted at the 2', 3' and/or 5' position, such as a —OH; —F; substituted or unsubstituted, linear or branched lower (Cl—ClO) alkyl, alkenyl, alkynyl, alkaryl, allyl, aryl, or aralkyl that may be interrupted by one or more heteroatoms; O-, S-, or N-alkyl; O-, S-, or N-alkenyl; O-, S- or N-alkynyl; O-, S-, or N-allyl; O-alkyl-0 alkyl, -methoxy, -aminopropoxy; -aminoxy; methoxyethoxy; -dimethylaminooxyethoxy; and -dimethylaminoethoxyethoxy. The sugar moiety can be a pyranose or derivative thereof, or a deoxypyranose or derivative thereof, preferably, a ribose or a derivative thereof, or a deoxyribose or a derivative thereof. Such preferred derivatized sugar moieties comprise Locked Nucleic Acid (LNA), in which the 2'-carbon atom is linked to the 3' or 4' carbon atom of the sugar ring, thereby, forming a bicyclic sugar moiety. A preferred LNA comprises 2'-0, 4'-C-ethylene-bridged nucleic acid (Morita et al. 2001, *Nucleic Acid Res Supplement No.* 1: 241-242). These substitutions render the nucleotide analogue, or equivalent RNase H and nuclease, resistant and increase the affinity for the target RNA. As is apparent to one of skill in the art, the substitutions provided herein render the double-stranded complex of the antisense oligonucleotide with its target pre-mRNA RNase H resistant. Accordingly, preferred oligonucleotides bind to the pre-mRNA of the protein to form a double-stranded nucleic acid complex and are chemically modified to render the double-stranded nucleic acid complex RNAse H resistant.

It is understood by a skilled person that it is not necessary for all positions in an antisense oligonucleotide to be modified uniformly. In addition, more than one of the aforementioned analogues or equivalents, may be incorporated in a single antisense oligonucleotide or even at a single position within an antisense oligonucleotide. In certain embodiments, an antisense oligonucleotide of the invention has at least two different types of analogues or equivalents.

As mentioned hereinabove, a preferred AON hereof, comprises a T-O alkyl phosphorothioate antisense oligonucleotide, such as 2'-O-methyl modified ribose (RNA), 2'-0-ethyl modified ribose, 2'-O-propyl modified ribose, and/or substituted derivatives of these modifications, such as halogenated derivatives. A most preferred AON, comprises of 2'-0-methyl phosphorothioate ribose.

An AON can be linked to a moiety that enhances uptake of the antisense oligonucleotide in cells. Examples of such moieties are cholesterols, carbohydrates, vitamins, biotin, lipids, phospholipids, cell-penetrating peptides including but not limited to antennapedia, TAT, transportan and positively charged amino acids, such as oligoarginine, poly-arginine, oligolysine or polylysine, antigen-binding domains, such as provided by an antibody, a Fab fragment of an antibody, or a single chain antigen binding domain, such as a cameloid single domain antigen-binding domain.

Preferably, additional flanking sequences are used to modify the binding of a protein to the AON, or to modify a thermodynamic property of the AON, more preferably, to modify target RNA binding affinity.

AON administration in humans is typically well tolerated. Clinical manifestations of the administration of AON in human clinical trials have been limited to the local side effects following subcutaneous (SC) injection (on the whole intravenous (i.v.) administration seems to be better tolerated) and generalized side effects, such as fever and chills that similar to the response to interferon administration, respond well to paracetamol. More than 4000 patients with different disorders have been treated so far using systemic delivery of first generation AON (phosphorothioate backbone), and approximately 500 following local administration. The typical dosage used ranged from 0.5 mg/kg every other day for one month in Crohn's disease, to 200 mg twice weekly for three months in rheumatoid arthritis, to higher dosages of 2 mg/kg day in other protocols dealing with malignancies. Fewer patients (approx. 300) have been treated so far using new generation AON (uniform phosphorothioated backbone with flanking 2' methoxyethoxy wing) delivered systemically at doses comprised between 0.5 and 9 mg/kg per week for up to three weeks.

Delivery of AON to cells of the brain can be achieved by various means. For instance, they can be delivered directly to the brain via intracerebral inoculation (Schneider et al., *Journal of Neuroimmunology* 195 (2008) 21-27), intraparenchymal infusion (Broaddus et al., J. Neurosurg. 1998 April; 88(4):734-42), intrathecal, or intraventricularly. Alternatively, the AON can be coupled to a single domain antibody or the variable domain thereof (VHH) that has the capacity to pass the Blood Brain barrier. Nanotechnology has also been used to deliver oligonucleotides to the brain, e.g., a nanogel consisting of cross-linked PEG and polyethylenimine. Encapsulation of AON in liposomes is also well known to one of skill in the art.

An AON hereof preferably comprises a sequence that is complementary to part of the pre-mRNA, as defined herein. In a more preferred embodiment, the length of the complementary part of the oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. Preferably, additional flanking sequences are used to modify the binding of a protein to the molecule or oligonucleotide, or to modify a thermodynamic property of the oligonucleotide, more preferably, to modify target RNA binding affinity. An AON of the invention may further comprise additional nucleotides that are not complementary to the target site on the target pre-mRNA. In a preferred embodiment, an AON contains between 8-50 nucleotides. An AON of the invention preferably comprises a stretch of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. In a preferred embodiment, the AON contains a continuous stretch of between 12-45 nucleotides, more preferably, a stretch of between 15-41 nucleotides. Depending on the chemistry of the backbone, as indicated hereinabove, an AON of the invention contains between 15-25 nucleotides. An AON of the invention with a morpholino backbone typically contains a stretch of between 25-40 nucleotides. In a preferred embodiment, the indicated amounts for the number of nucleotides in the AON refers to the length of the complementarity to the target pre-mRNA, preferably to an exon internal sequence, however, the target sequence can also be a 5' or a 3' splice site of an exon or an intron sequence, such as preferably a branch point. In another preferred embodiment, the indicated amounts refer to the total number of nucleotides in the AON.

Preferably, the complementary part is at least 50% of the length of the oligonucleotide of the invention, more preferably, at least 60%, even more preferably, at least 70%, even more preferably, at least 80%, even more preferably, at least 90% or even more preferably, at least 95%, or even more preferably, 98% and most preferably, up to 100% of the length of the oligonucleotide of the invention, with the putative exception of deliberately introduced specific mismatches, e.g., for down-regulating affinity when necessary.

With respect to AON that also contain additional nucleotides, the total number of nucleotides typically does not exceed 50, and the additional nucleotides preferably range in number from between 5-25, preferably from 10-25, more preferably, from 15-25. The additional nucleotides typically are not complementary to the target site on the pre-mRNA but may be complementary to another site on the pre-mRNA or may serve a different purpose and not be complementary to the target pre-mRNA, i.e., less then 95% sequence identity of the additional nucleotides to the reverse complement of the target pre-mRNA.

The proteolytic cleavage site that is to be removed from a protein by a method or AON of the invention is preferably a serine endoprotease cleavage site, a metaloendopeptidase cleavage site, a secretase cleavage site and/or a caspase cleavage site. In a particularly preferred embodiment, the cleavage site is a caspase cleavage site or secretase cleavage site. Caspases are a family of intracellular cysteine proteases that play a central role in the initiation and execution of programmed cell death. The term caspases is a short form for Cystein Aspartate-specific Proteases: their catalytical activity depends on a critical cystein-residue within a highly conserved active-site pentapeptide QACRG, and the caspases specifically cleave their substrates after Asp residues (also the serine-protease granzyme B has specificity for Asp in the P1 position of substrates). More than ten different members of the caspase family have been identified in mammals. According to a unified nomenclature, the caspases are referred to in the order of their publication: so Caspase-1 is ICE (Interleukin-1beta-Converting Enzyme), the first aspartate-specific cystein protease described. The secretase family of proteases is subdivided into three groups, the alpha-, beta- and gamma-secretases. In a preferred embodiment, the secretase is a gamma-secretase.

The protein from which the proteolytic cleavage site is to be removed can be any protein that contains a proteolytic cleavage site. In a preferred embodiment, the protein is a mammalian protein, more preferably, a primate protein. In a particularly preferred embodiment, the protein is a human protein. In a preferred embodiment, the protein is associated with a disease in humans. In a particularly preferred embodiment, the protein is associated with a triplet repeat disease in humans. Preferably, a polyglutamine repeat disease.

In a preferred embodiment, the protein comprises a caspase cleavage site or secretase cleavage site. Preferably, the protein comprises a caspase-3 or -6 proteolytic cleavage site. Preferably, the protein is a protein that is normally present in the brain of a mammal. In a particularly preferred embodiment, the gene encoding the protein is a mutant gene that encodes a trinucleotide repeat expansion when compared to the gene of a normal individual.

In a particularly preferred embodiment, the protein is a protein encoded by one of the genes listed in table 1a or 1b. In a particularly preferred embodiment, the gene is a mutant gene that is the causative gene in a polyglutamine disorder, preferably a gene of table 1a. In a particularly preferred embodiment, the gene is the huntingtin (Htt) gene. Htt is expressed in all mammalian cells. The highest concentrations are found in the brain and testes, with moderate amounts in the liver, heart, and lungs. The function of Htt in humans is as yet not entirely resolved. Htt interacts among others with proteins, which are involved in transcription, cell signaling and intracellular transporting. In humans the gene, and in particular mutants thereof, is associated with Huntington's disease (HD). HD is a progressive neurodegenerative genetic disorder, which affects muscle movement and muscle coordination and leads to cognitive decline and dementia. It typically becomes noticeable in middle age. HD is the most common genetic cause of abnormal involuntary writhing movements called chorea and is much more common in people of Western European descent than in those from Asia or Africa. The disease is caused by an autosomal dominant mutation of the Htt-gene. A child of an affected parent has a 50% risk of inheriting the disease.

For the Htt gene it is preferred that the caspase-6 proteolytic cleave site encoded by exon Htt exon 12 is removed from the Huntingtin protein. It is preferred that the coding region that codes for the proteolytic cleavage site is removed "in frame," so as to allow incorporation of the normal downstream amino acid sequence into the mutant protein. In one embodiment, the "in frame" removal is achieved by providing the cell with an AON that enables skipping of exon 12 and an AON that enables skipping of exon 13 of the Htt gene. In another preferred embodiment, the "in frame" removal is achieved by providing the cell with an AON capable of inducing exon skipping directed toward the region delimited by nucleotides 269-297 of exon 12 of the Htt gene. In a preferred embodiment, the AON is directed toward region delimited by nucleotides 207 until 341 of exon 12. It is preferred that the AON is directed toward the internal region delimited by nucleotides 207 until 341 of exon 12. This includes nucleotides 207 and 341. It has been found in the present invention that AON directed toward the preferred regions induce skipping of the last 135 nucleotides of exon 12, thereby producing an "in frame" complete deletion of two active caspase 3 cleavage sites at amino acid 513 and 552, and removal of the first amino acid of an active caspase 6 site, partially located in exon 12 and partially in exon 13. AON HDEx12_1 (table 2) activates a cryptic splice site at nucleotide 206 in exon 12, leading to the absence of the remainder of exon 12 from the formed mRNA.

Further provided is an isolated and/or recombinant modified Htt mRNA having a deletion of at least nucleotides 207 until 341 of exon 12. The modified Htt mRNA preferably comprises the exons 1-11, the first 206 nucleotides of exon 12 and exons 13-67. In another preferred embodiment, the modified Htt mRNA comprises the exons 1-11, 14-67.

In another embodiment provided is an isolated and/or recombinant modified Htt protein comprising a deletion of amino acids 538-583. The modified Htt protein preferably comprises the amino acid sequence encoded by exons 1-11, the first 206 nucleotides of exon 12, and exons 13-67. In another preferred embodiment, the modified Htt protein comprises the amino acid sequence encoded by exons 1-11, 14-67.

In yet another embodiment provided is an isolated and/or recombinant cell comprising a modified Htt mRNA and/or a modified Htt protein as indicated herein above. Preferably, the cell comprises an Htt gene comprising a coding region of a polyglutamine repeat, the length of which is associated with HD.

For the ATXN3 gene, it is preferred that the caspase cleavage sites in exon 7 is removed from the protein. It is preferred that the coding region that codes for the proteolytic cleavage site is removed "in frame," so as to allow incorporation of the normal downstream amino acid into the mutant protein. In one embodiment, the "in frame" removal is achieved by providing the cell with an AON that enables skipping of exon 7 and an AON that enables skipping of exon 8 of the ATXN3 gene.

For the ATN1 gene it is preferred that the caspase 3 cleavage site near the N-terminus of the protein and the polyglutamine tract ($^{106}$DSLD$^{109}$) in exon 5 is removed from the protein. It is preferred that the coding region that codes for the proteolytic cleavage site is removed "in frame," so as to allow incorporation of the normal downstream amino acid into the mutant protein. In one embodiment, the "in frame" removal is achieved by providing the cell with an AON that enables skipping of exon 5 and an AON that enables skipping of exon 6 of the ATN1 gene. In a preferred embodiment, the AON comprises a sequence as depicted in table 2 under DPRLA AON.

Further provided is an AON hereof, of preferably between 14-40 nucleotides, that induces skipping of an exon that encodes a proteolytic cleavage site in a protein. In a preferred embodiment, provided is an AON, as indicated hereinabove, comprising a sequence as depicted in Table 2. The AON is suitable for skipping the indicated exon of the gene. In a particularly preferred embodiment, the AON comprises the sequence of HDEx12_1 of table 2. In another preferred embodiment, provided is an AON as indicated herein above that is specific for the region identified by a sequence of an AON depicted in table 2. In a preferred embodiment, the AON comprises at least 10 consecutive nucleotides of the region identified by an oligonucleotide as depicted in table 2. In a particularly preferred embodiment, provided is an AON, as indicated hereinabove, that is specific for the region identified by a sequence of HDEx12_1 of Table 2.

Further provided is the use of exon-skipping in a cell for removing a proteolytic cleavage site from a protein. Further provided is the use of an AON that induces skipping of an exon that encodes a proteolytic cleavage site in a protein, for removing the proteolytic cleavage site from the protein in a cell that produces pre-mRNA encoding the protein. Further provided si an oligonucleotide of between 14-40 nucleotides that induces skipping of an exon that encodes a proteolytic cleavage site in a protein for use in the treatment of a disease that is associated with a proteolytic cleavage product of the protein.

In another embodiment, provided is a method for altering the proteolytic processing of a protein that comprises a proteolytic cleavage site comprising providing a cell that produces a pre-mRNA that codes for the protein with an AON that is specific for the pre-mRNA; and that prevents inclusion of the code for the proteolytic cleavage site into mature mRNA produced from the pre-mRNA, the method further comprising allowing translation of the mRNA to produce the protein of which the proteolytic processing is altered.

Further provided is a non-human animal comprising an oligonucleotide hereof. Preferably, the non-human animal comprises a mutant gene that encodes a trinucleotide repeat expansion when compared to the gene of a normal individual.

Further provided is a modified human protein from which a proteolytic cleavage site is removed by means of exon skipping. Further provided is an mRNA encoding a modified human protein from which a proteolytic cleavage site is removed by means of exon skipping.

Further provided is a cell encoding a human protein comprising a proteolytic cleavage site, wherein the cell contains an AON of the invention for removing the proteolytic cleavage site from the protein in the cell.

The general nomenclature of cleavage site positions of the substrate were formulated by Schecter and Berger, 1967-68 [Schechter and Berger, 1967], [Schechter and Berger, 1968]. They designate the cleavage site between P1-P1', incrementing the numbering in the N-terminal direction of the cleaved peptide bond (P2, P3, P4, etc.). On the carboxyl side of the cleavage site, numbering are likewise incremented (P1', P2', P3', etc.).

BRIEF DESCRIPTION OF THE DRAWINGS

FIG. 4: Partial amino acid sequence of the huntingtin protein (see SEQ ID NO:227). Underlined are the amino acids encoded by exon 12 and 13. Highlighted is the part of the protein that is currently skipped by the exon 12 AON. In bold is the caspase-3 site $^{510}$DSVD$^{513}$, caspase-3 site $^{549}$DLND$^{552}$ and caspase-6 site $^{583}$IVLD$^{586}$.

DETAILED DESCRIPTION

Examples

Figures 1A, 1B:
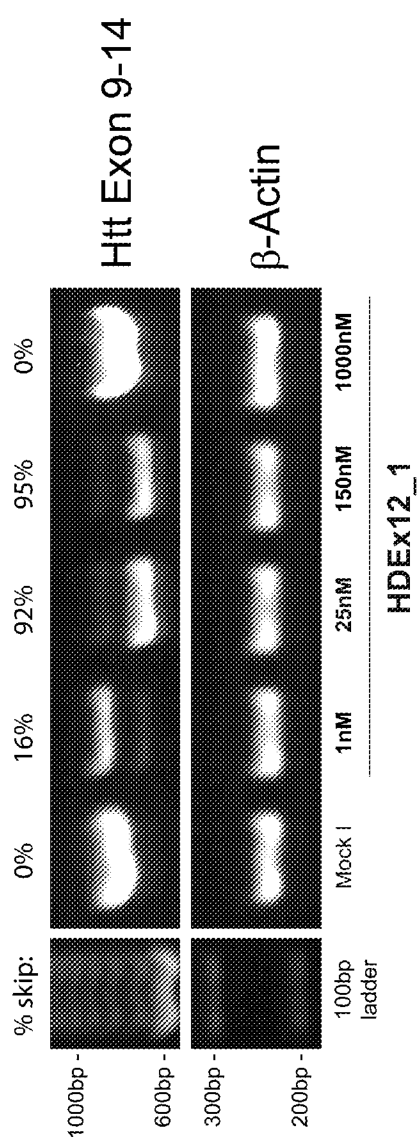
FIG. 1: Exon skipping after transfection with various concentrations HDEx12_1 AON. A) Patient derived HD fibroblasts were treated with 1, 25, 150, and 1000 nM HDEx12_1. β-Actin was taken along as loading control. Increasing the AON concentration from 1 nM to 25 nM resulted in a higher skip percentage from 16% to 92% as was measured by Lab-on-a-Chip. The highest skip percentage of 95% was obtained with 150 nM HDEx12_1. Too high concentration of AON resulted in inefficient skip. In the Mock I control (transfection agent only) no skip is visible as expected. The potency of HDEx12_1 exon 12 skip was also seen in another HD and control fibroblast cell line and human neuroblastoma SH-SY5Y cells. B) Schematic representation of PCR of HD exons 9 to 14. Both schematic representation of normal (top) and shorter, skipped exon 12 (bottom) products are shown.

AON-mediated exon skipping in neurodegenerative diseases to remove proteolytic cleavage sites. AON-mediated exon skipping in Huntington's disease to remove proteolytic cleavage sites from the huntingtin protein Methods AONs and Primers All AONs consisted of 2'-O-methyl RNA and full length phosphorothioate backbones.

Cell Cultures and AON Transfection

Patient fibroblast cells and human neuroblastoma cells were transfected with AONs at concentrations ranging between 1-1000 nM, using Polyethylenemine (PEI) ExGen500 according to the manufacturer's instructions, with 3.3 µl PEI per µg of transfected AON. A second transfection was performed 24 hours after the first transfection. RNA was isolated 24 hours after the second transfection and cDNA was synthesized using random hexamer primers.

Cell Lines Used:

FLB73 Human Fibroblast Control
GM04022 Human Fibroblast HD
GM02173 Human Fibroblast HD
SH-SY5Y Neuroblastoma Control Quantitative Real-Time PCR (qRT-PCR) was carried out using the LightCycler® 480 System (Roche) allowing for quantification of gene expression.

Agarose Gel and Sanger Sequencing

All PCR products were run on 2% agarose gel with 100 base pair ladders. Bands were isolated using the QIAgen® PCR purification kit according to manufacturer's instructions. The samples were then sequenced by Sanger sequencing using the Applied Biosystems BigDyeTerminator v3.1 kit.

Lab-on-a-Chip

Lab-on-a-Chip automated electrophoresis was used to quantify the PCR products using a 2100 Bioanalyzer. Samples were made 1 part β-Actin primed product, as a reference transcript, to 5 parts experimental PCR products. The samples were run on a DNA 1000 chip.

Western Blot

Protein was isolated from cells 72 hours after the first transfection and run on a Western blots, transferred onto a PVDF membrane and immunolabelled with primary antibodies recognizing htt, 1H6 or 4C8 (both 1:1,000 diluted)

Materials

AONs and primers were obtained from Eurogentec, Liege, Belgium.

AON sequences:

```
HDEx12_1:
                                (SEQ ID NO: 1)
CGGUGGUGGUCUGGGAGCUGUCGCUGAUG

HDEx12_2:
                                (SEQ ID NO: 2)
UCACAGCACACACUGCAGG

HDEx13_1:
                                (SEQ ID NO: 3)
GUUCCUGAAGGCCUCCGAGGCUUCAUCA

HDEx13_2:
                                (SEQ ID NO: 4)
GGUCCUACUUCUACUCCUUCGGUGU
```

Patient fibroblast cell lines GM04022 and GM02173 were obtained from Coriell, Institute for Medical Research, Camden, USA and control fibroblast cell line FLB73 from Maaike Vreeswijk, LUMC.

Results

Figure 2:
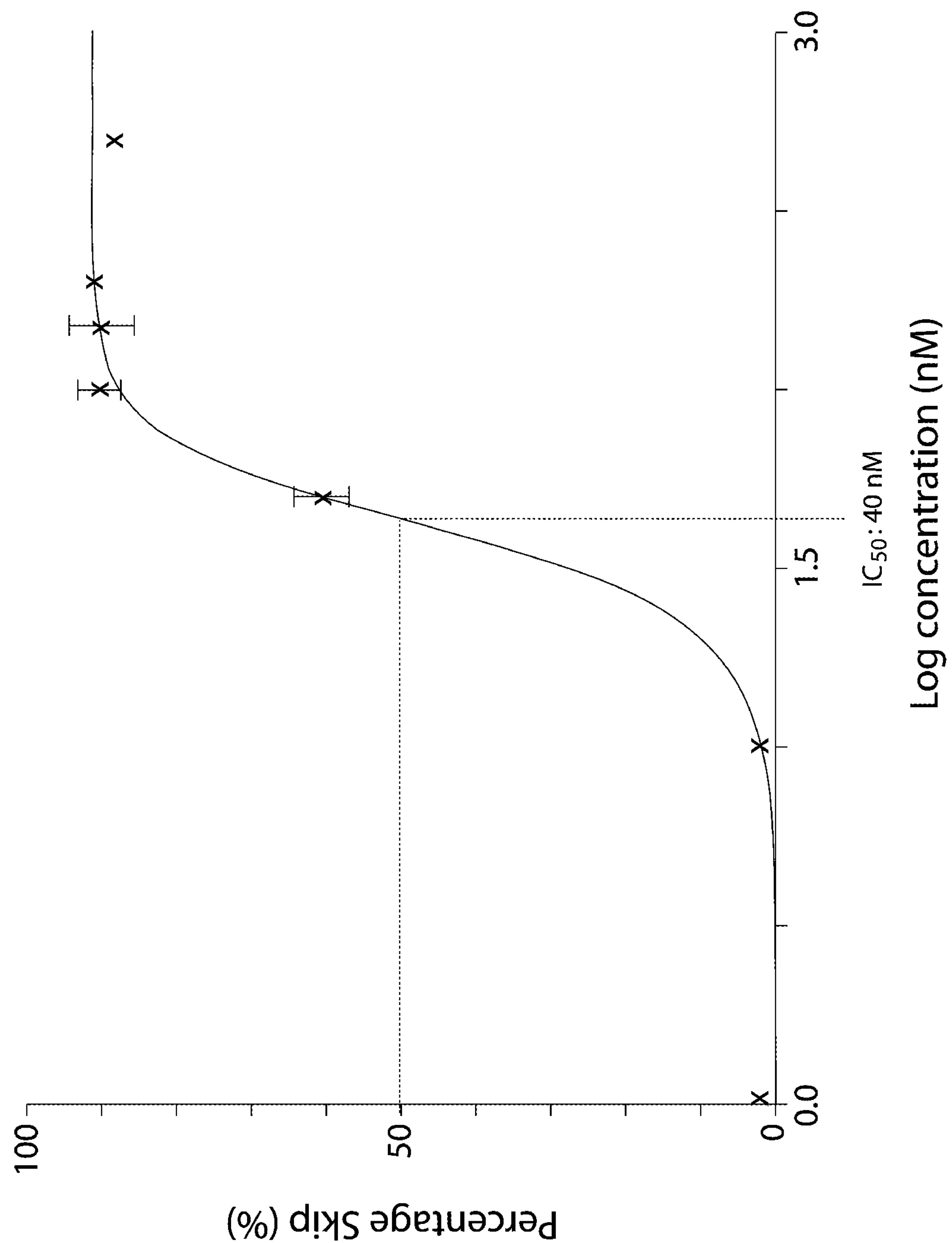
FIG. 2: Log dose response curve of HDEx12_1 AON in a HD fibroblast cell line. X-axis displays the log concentration (nM) and y-axis the percentage of skip. The half maximum inhibitory value (IC50) of the HDEx12_1 AON was found to be 40 nM. The optimal percentage exon 12 skip was achieved with an AON concentration of 150 nM and higher. Results shown as mean±SEM (n=2-3).
Figure 3A:
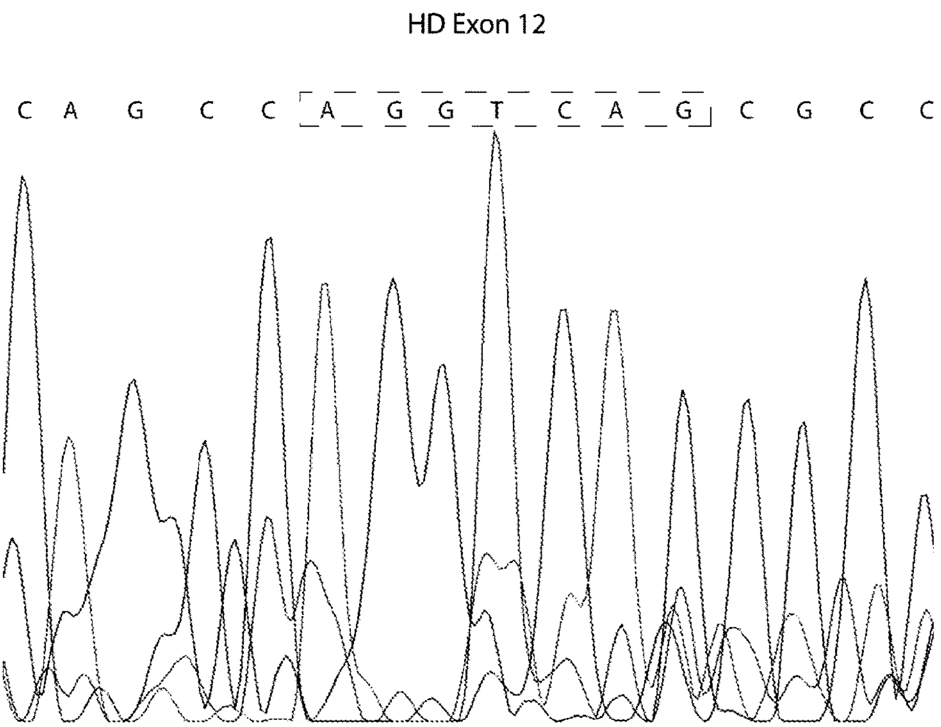
FIG. 3: Sanger sequencing of normal (A) and skipped (SEQ ID NO:228) (B) PCR product (SEQ ID NO:229). HDEx12_1 AON transfection in a HD fibroblast cell line resulted in an in-frame skip of 135 nucleotides, which corresponds with 45 amino acids. The observed skip is caused by the activation of an alternative splice site (AG|GTRAG, see dashed box (positions 6-12 of SEQ ID NO:228)), resulting in an alternative splice site exon isoform. This partial exon 12 skip results in the deletion of an active caspase-3 site $^{549}$DLND$^{552}$ and partial removal of the first amino acid (Isoleucine) of an active caspase-6 site ($^{583}$IVLD$^{586}$).
Figure 3B:
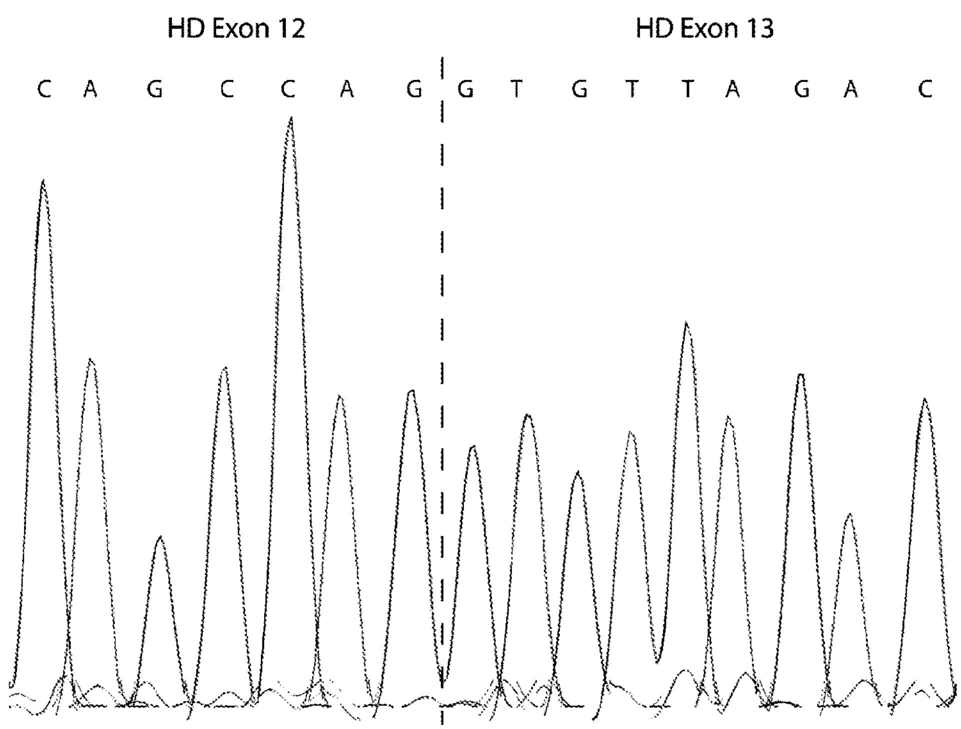
Figure 5A:
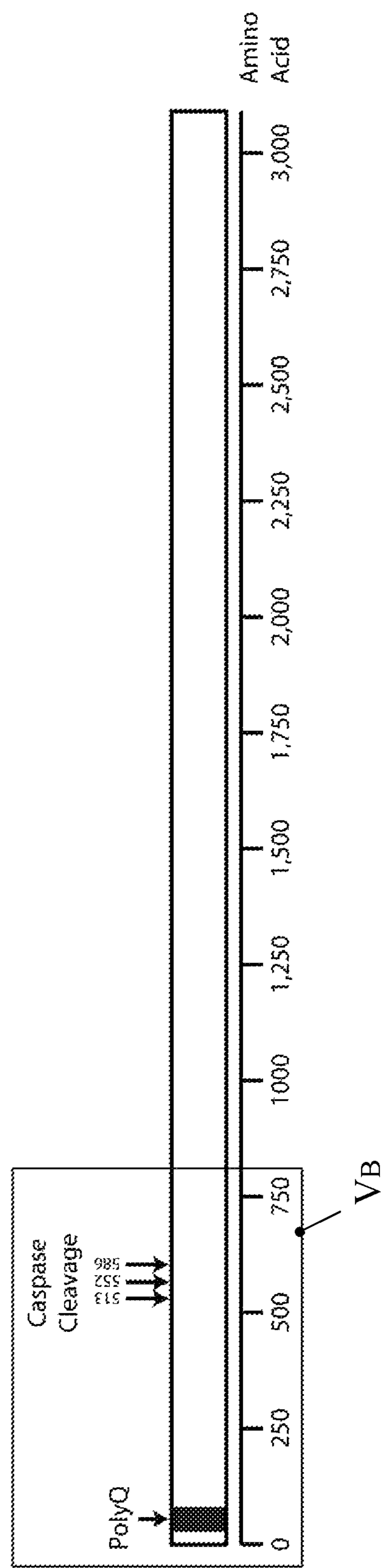
FIG. 5: Schematic diagram of huntingtin. A) Diagram of complete htt protein. PolyQ indicates the polyglutamine tract. The arrows indicate the caspase cleavage sites and their amino acid positions. B) Amino-terminal part of the htt protein. Htt exon 1 to 17 are depicted. The arrows indicate the caspase cleavage sites and their amino acid positions. C) Schematic representation and amino acid sequence of htt exon 12 and 13 with the caspase cleavage motifs depicted in bold. Exon boundaries are shown with vertical grey bars (SEQ ID NO:230). D) Partial amino acid and nucleotide sequence of htt exon 12 and 13 (SEQ ID NOS:231 and 233). Caspase cleavage motifs are depicted in bold and exon boundary is shown with vertical grey bar. The light grey highlighted sequence denotes the part which is skipped after HDEx12_1 AON treatment.
Figure 5B:
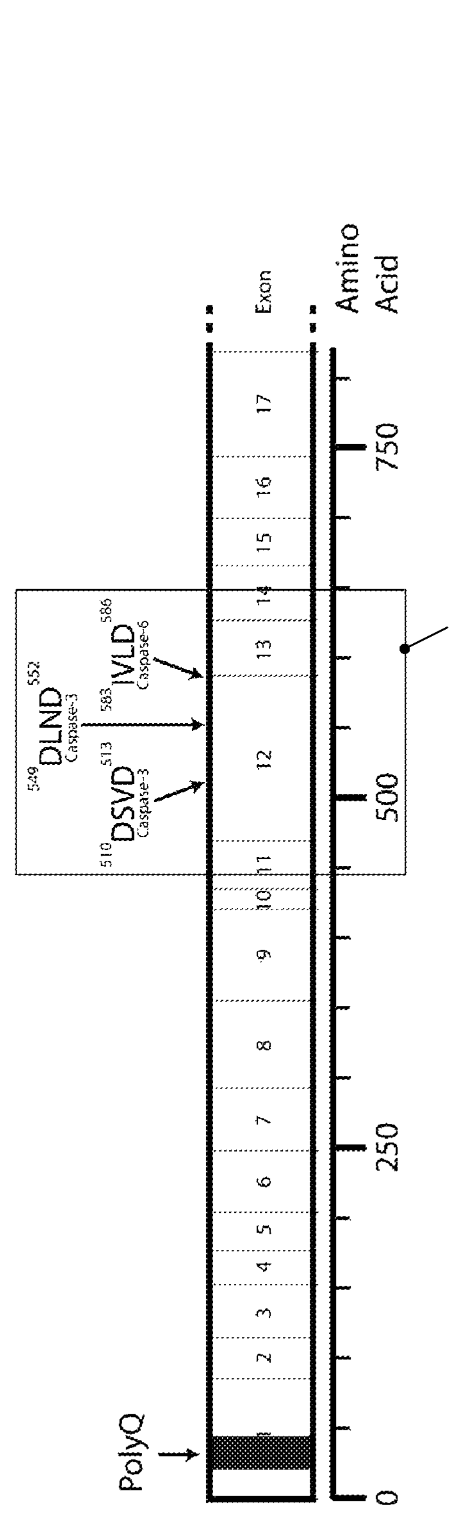
Figures 5C, 5D:
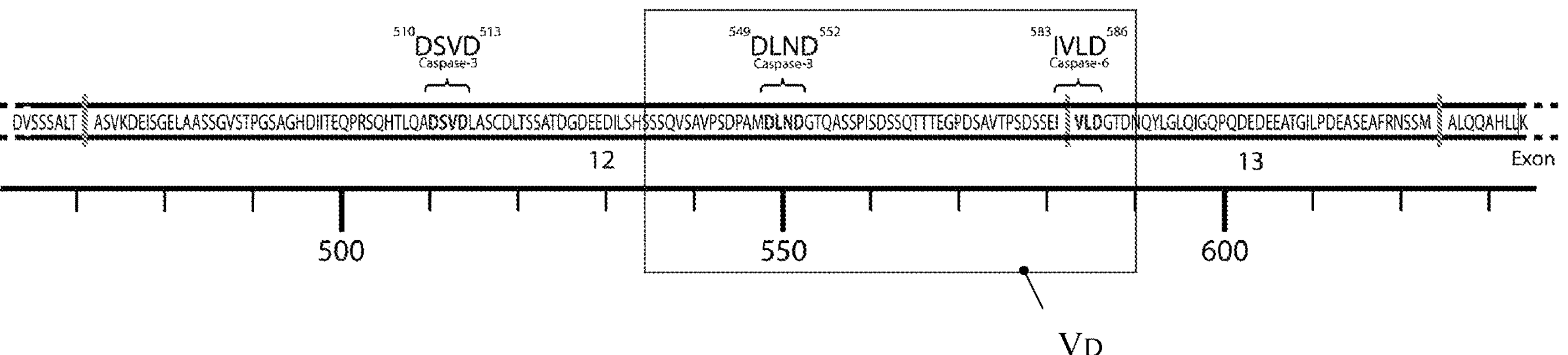

Transfection of AON HDEx12_1 in both patient derived HD fibroblast and human neuroblastoma cells showed an efficient skip (see FIG. 1) of exon 12. The optimal percentage exon 12 skip was achieved with a concentration of 150 nM, but a skip was already visible at 1 nM (see FIG. 2). Sanger sequencing confirmed that the last 135 nucleotides of exon 12 were skipped after transfection of the cells with AON HDEx12_1. This corresponded to deletion of 45 amino acids containing two active caspase 3 sites and the first amino acid of an active caspase 6 site (see FIGS. 3 and 4). In silico analysis revealed that the observed skip is likely due to the activation of the alternative splice site AG|G-TRAG (positions 6-12 of SEQ ID NO:228) resulting in an alternative splice site exon isoform (see FIG. 3).

CONCLUSIONS

With AON HDEx12_1, we have shown a partial skip of exon 12 of the huntingtin transcript that result in a truncated but in frame protein product. Using different cell lines we have confirmed this partial exon 12 skip by Sanger sequencing and in silico analysis revealed an alternative splice site in exon 12 that is likely the cause of this partial skip. This skipped protein product misses two complete caspase-3 cleavage sites located in exon 12, and the first amino acid of the caspase-6 cleavage site that is located on the border of exon 12 and 13. Recent mouse model data showed that the preferred site of in vivo htt cleavage to be at amino acid 552, which is used in vitro by either caspase-3 or caspase-2 [1] and that mutation of the last amino acid of the caspase 6 cleavage site at amino acid position 586 reduces toxicity in an HD model [2].

Functional analysis will be performed to determine whether AON HDEx12_1 can reduce the toxicity of mutant huntingtin and to determine the level of prevention of formation of toxic N-terminal huntingtin fragments. Also other AONs will be tested to completely skip exons 12 and 13 of the huntingtin transcript.

REFERENCES CITED

1. Wellington, C. L. et al. Inhibiting caspase cleavage of huntingtin reduces toxicity and aggregate formation in neuronal and nonneuronal cells. *J. Biol. Chem.* 275, 19831-19838 (2000).
2. Graham, R. K. et al. Cleavage at the Caspase-6 Site Is Required for Neuronal Dysfunction and Degeneration Due to Mutant Huntingtin. *Cell* 125, 1179-1191 (2006).

TABLE 1a

| Polyglutamine (PolyQ) Diseases | | | |
|---|---|---|---|
| Type | Gene | Normal PolyQ repeats | Pathogenic PolyQ repeats |
| DRPLA (Dentatorubropallidoluysian atrophy) | ATN1 or DRPLA | 6-35 | 49-88 |
| HD (Huntington's disease) | Htt (Huntingtin) | 10-35 | 35+ |
| SBMA (Spinobulbar muscular atrophy or Kennedy disease) | Androgen receptor on the X chromosome. | 9-36 | 38-62 |
| SCA1 (Spinocerebellar ataxia Type 1) | ATXN1 | 6-35 | 49-88 |
| SCA2 (Spinocerebellar ataxia Type 2) | ATXN2 | 14-32 | 33-77 |
| SCA3 (Spinocerebellar ataxia Type 3 or Machado-Joseph disease) | ATXN3 | 12-40 | 55-86 |
| SCA6 (Spinocerebellar ataxia Type 6) | CACNA1A | 4-18 | 21-30 |
| SCA7 (Spinocerebellar ataxia Type 7) | ATXN7 | 7-17 | 38-120 |
| SCA17 (Spinocerebellar ataxia Type 17) | TBP | 25-42 | 47-63 |

TABLE 1b

| Non-Polyglutamine Diseases<br>Unstable repeat disorders caused by loss-of-function, RNA-mediated, or unknown mechanism | | | | | | |
|---|---|---|---|---|---|---|
| Disease | MIM Number | Repeat unit | Gene product | Normal repeat | Expanded repeat | Main clinical features length |
| Loss of function mechanism | | | | | | |
| FRAXA | 309550 | $(CGC)_n$ | FMRP | 6-60 | >200 (full mutation) | Mental retardation, macroorchidsm, connective tissue defects, behavioral abnormalities |
| FRAXE | 309548 | $(CCG)_n$ | FMR2 | 4-39 | 200-900 | Mental retardation |
| FRDA | 229300 | $(GAA)_n$ | Frataxin | 6-32 | 200-1700 | Sensory ataxia, cardiomyopathy, diabetes |
| RNA-mediated pathogenesis | | | | | | |
| DM1 | 160900 | $(CTG)_n$ | DMPK | 5-37 | 50-10,000 | Myotonia, weakness, cardiac conduction defects, insulin resistance, cataracts, testicular atrophy, and mental retardation in congenital form |
| FXTAS | 309550 | $(CGG)_n$ | FMR1 RNA | 6-60 | 60-200 (premutation) | Ataxia, tremor, Parkinsonism, and |

TABLE 1b-continued

| Non-Polyglutamine Diseases<br>Unstable repeat disorders caused by loss-of-function, RNA-mediated, or unknown mechanism | | | | | | |
|---|---|---|---|---|---|---|
| Disease | MIM Number | Repeat unit | Gene product | Normal repeat | Expanded repeat | Main clinical features length |
| | | | | | | dementia |
| Unknown pathogenic mechanism | | | | | | |
| SCA8 | 608768 | $(CTG)_n$ | SCA8 RNA | 16-34 | >74 | Ataxia, slurred speech, nystagmus |
| SCA12 | 604326 | $(CAG)_n$ | PPP2R2B | 7-45 | 55-78 | Ataxia and seizures |
| HDL2 | 606438 | $(CTG)_n$ | Junctophilin | 7-28 | 66-78 | Similar to HD |

Annual Review of Neuroscience Vol. 30: 575-621 (Volume publication date July 2007) Trinucleotide Repeat Disorders Harry T. Orr and Huda Y. Zoghbi

TABLE 2

List of AON

HDEx12_1: CGGUGGUGGUCUGGGAGCUGUCGCUGAUG (SEQ ID NO: 1)

HDEx12_2: UCACAGCACACACUGCAGG (SEQ ID NO: 2)

HDEx13_1: GUUCCUGAAGGCCUCCGAGGCUUCAUCA (SEQ ID NO: 3)

HDEx13_2: GGUCCUACUUCUACUCCUUCGGUGU (SEQ ID NO: 4)

HDEx12_2 is a comparative example of an oligonucleotide having the nucleotide sequence of Htt in the sense strand.

DRPLA AONs:

1 DRPLAEx5_18 GUC GCU GCU GCC AUC AUC AU (SEQ ID NO: 5)

2 DRPLAEx5_128 AAG AGG AAG CAG GAG GCA GA (SEQ ID NO: 6)

3 DRPLAEx5_81 GGA GGA GCC UGG AAC AUU CG (SEQ ID NO: 7)

1 DRPLAEx6_80 AAG CUC GCG CUC CUU CUC GC (SEQ ID NO: 8)

2 DRPLAEx6_1 CGA GUU GAA GCC GCG AUC CA (SEQ ID NO: 9)

3 DRPLAEx6_84 GUU CAA GCU CGC GCU CCU UC (SEQ ID NO: 10)

HDEx AON are oligonucleotides for skipping exons 12 or 13 of the Htt gene.
DRPLA AON are oligonucleotides for skipping exons 5 or 6 of the DRPLA/ATN1 gene.

Table 3 provides further oligonucleotides for exon skipping.

APP: amyloid precursor protein in Alzheimer's disease (AD); ATN1: Atrophin 1 in DRPLA; ATNX3: Ataxin 3 for SCA3; ATXN7: Ataxin 7 in SCAT; TBP: TATA binding protein for SCA17; and HTT in Huntington's disease (HD)

TABLE 3

| Disease | AON Name | Target Sequence | SEQ ID NO: | AON Sequence | SEQ ID NO: |
|---|---|---|---|---|---|
| AD | hAPPEx15_1 | GTTCTGGGTTGACAAATATCAAG | 11 | CUUGAUAUUUGUCAACCCAGAAC | 12 |
| AD | hAPPEx15_2 | CGGAGGAGATCTCTGAAGTGAAG | 13 | CUUCACUUCAGAGAUCUCCUCCG | 14 |
| AD | hAPPEx15_3 | GATGCAGAATTCCGACATGAC | 15 | GUCAUGUCGGAAUUCUGCAUC | 16 |
| AD | hAPPEx15_4 | CTCAGGATATGAAGTTCATCATC | 17 | GAUGAUGAACUUCAUAUCCUGAG | 18 |
| AD | hAPPEx16_1 | GCAATCATTGGACTCATGGT | 19 | ACCAUGAGUCCAAUGAUUGC | 20 |
| AD | hAPPEx16_2 | GATCGTCATCACCTTGGTGA | 21 | UCACCAAGGUGAUGACGAUC | 22 |

AON sequences targeting proteins involved in neurodegenerative diseases

TABLE 3-continued

AON sequences targeting proteins involved in neurodegenerative diseases

| Disease | AON Name | Target Sequence | SEQ ID NO: | AON Sequence | SEQ ID NO: |
|---|---|---|---|---|---|
| AD | hAPPEx16_3 | GTACACATCCATTCATCATGGTG | 23 | CACCAUGAUGAAUGGAUGUGUAC | 24 |
| AD | hAPPEx16_4 | GCAGAAGATGTGGGTTCAAAC | 25 | GUUUGAACCCACAUCUUCUGC | 26 |
| AD | hAPPEx16_5 | GGTGATGCTGAAGAAGAAACAG | 27 | CUGUUUCUUCUUCAGCAUCACC | 28 |
| AD | hAPPEx16_6 | TCATCATGGTGTGGTGGAGGTAG | 29 | CUACCUCCACCACACCAUGAUGA | 30 |
| DRPLA | hATN1Ex5_1 | CTCCCTCGGCCACAGTCTCCCT | 31 | AGGGAGACUGUGGCCGAGGGAG | 32 |
| DRPLA | hATN1Ex5_2 | GCGGAGCCTTAATGATGATGGC | 33 | GCCAUCAUCAUUAAGGCUCCGC | 34 |
| DRPLA | hATN1Ex5_3 | AGCAGCGACCCTAGGGATATCG | 35 | CGAUAUCCCUAGGGUCGCUGCU | 36 |
| DRPLA | hATN1Ex5_4 | AGGACAACCGAAGCACGTCCC | 37 | GGGACGUGCUUCGGUUGUCCU | 38 |
| DRPLA | hATN1Ex5_5 | TGGAAGTGTGGAGAATGACTCTG | 39 | CAGAGUCAUUCUCCACACUUCCA | 40 |
| DRPLA | hATN1Ex5_6 | ATCTTCTGGCCTGTCCCAGGGC | 41 | GCCCUGGGACAGGCCAGAAGAU | 42 |
| DRPLA | hATN1Ex5_7 | CGACAGCCAGAGGCTAGCTTTGA | 43 | UCAAAGCUAGCCUCUGGCUGUCG | 44 |
| DRPLA | hATN1Ex5_8 | CTCGAATGTTCCAGGCTCCTCC | 45 | GGAGGAGCCUGGAACAUUCGAG | 46 |
| DRPLA | hATN1Ex5_9 | TCTATCCTGGGGGCACTGGTGG | 47 | CCACCAGUGCCCCCAGGAUAGA | 48 |
| DRPLA | hATN1Ex5_10 | TGGACCCCCAATGGGTCCCAAG | 49 | CUUGGGACCCAUUGGGGGUCCA | 50 |
| DRPLA | hATN1Ex5_11 | AGGGGCTGCCTCATCAGTGG | 51 | CCACUGAUGAGGCAGCCCCU | 52 |
| DRPLA | hATN1Ex5_12 | AAGCTCTGGGGCTAGTGGTGCTC | 53 | GAGCACCACUAGCCCCAGAGCUU | 54 |
| DRPLA | hATN1Ex5_13 | ACAAAGCCGCCTACCACTCCAG | 55 | CUGGAGUGGUAGGCGGCUUUGU | 56 |
| DRPLA | hATN1Ex5_14 | CTCCACCACCAGCCAACTTCC | 57 | GGAAGUUGGCUGGUGGUGGAG | 58 |
| DRPLA | hATN1Ex5_15 | CCAACCACTACCTGGTCATCTG | 59 | CAGAUGACCAGGUAGUGGUUGG | 60 |
| DRPLA | hATN1Ex5_16 | TGGCCCAGAGAAGGGCCCAAC | 61 | GUUGGGCCCUUCUCUGGGCCA | 62 |
| DRPLA | hATN1Ex5_17 | TTCCTCTTCTGCTCCAGCGCC | 63 | GGCGCUGGAGCAGAAGAGGAA | 64 |
| DRPLA | hATN1Ex5_18 | GTTTCCTTATTCATCCTCTAG | 65 | CUAGAGGAUGAAUAAGGAAAC | 66 |
| DRPLA | hATN1Ex5_19 | GCCTCTCTGTCTCCAATCAGC | 67 | GCUGAUUGGAGACAGAGAGGC | 68 |
| DRPLA | hATN1Ex5_20 | CCATCCCAGGCTGTGTGGAG | 69 | CUCCACACAGCCUGGGAUGG | 70 |
| DRPLA | hATN1Ex5_21 | TCTACTGGGGCCCAGTCCACCG | 71 | CGGUGGACUGGGCCCCAGUAGA | 72 |
| DRPLA | hATN1Ex5_22 | GCATCACGGAAACTCTGGGCC | 73 | GGCCCAGAGUUUCCGUGAUGC | 74 |
| DRPLA | hATN1Ex5_23 | CCACTGGAGGGCGGTAGCTCC | 75 | GGAGCUACCGCCCUCCAGUGG | 76 |
| DRPLA | hATN1Ex5_24 | CTCCCTGGGGTCTCTGAGGCC | 77 | GGCCUCAGAGACCCCAGGGAG | 78 |
| DRPLA | hATN1Ex5_25 | CACCAGGGCCAGCACACCTGC | 79 | GCAGGUGUGCUGGCCCUGGUG | 80 |
| DRPLA | hATN1Ex5_26 | GTGTCCTACAGCCAAGCAGGCC | 81 | GGCCUGCUUGGCUGUAGGACAC | 82 |
| DRPLA | hATN1Ex5_27 | CAAGGGTCCTACCCATGTTCAC | 83 | GUGAACAUGGGUAGGACCCUUG | 84 |
| DRPLA | hATN1Ex5_28 | CACCGGTGCCTACGGTCACCAC | 85 | GUGGUGACCGUAGGCACCGGUG | 86 |
| DRPLA | hATN1Ex5_29 | CTCTTCGGCTACCCTTTCCAC | 87 | GUGGAAAGGGUAGCCGAAGAG | 88 |
| DRPLA | hATN1Ex5_30 | GGTCATTGCCACCGTGGCTTC | 89 | GAAGCCACGGUGGCAAUGACC | 90 |
| DRPLA | hATN1Ex5_31 | CCACCGTACGGAAAGAGAGCC | 91 | GGCUCUCUUUCCGUACGGUGG | 92 |
| DRPLA | hATN1Ex5_32 | CCACCGGGCTATCGAGGAACCTC | 93 | GAGGUUCCUCGAUAGCCCGGUGG | 94 |
| DRPLA | hATN1Ex5_33 | CAGGCCCAGGGACCTTCAAGCC | 95 | GGCUUGAAGGUCCCUGGGCCUG | 96 |

TABLE 3-continued

AON sequences targeting proteins involved in neurodegenerative diseases

| Disease | AON Name | Target Sequence | SEQ ID NO: | AON Sequence | SEQ ID NO: |
|---|---|---|---|---|---|
| DRPLA | hATN1Ex5_34 | CCACCGTGGGACCTGGGCCCCTG | 97 | CAGGGGCCCAGGUCCCACGGUGG | 98 |
| DRPLA | hATN1Ex5_35 | GCCACCTGCGGGGCCCTCAGGC | 99 | GCCUGAGGGCCCCGCAGGUGGC | 100 |
| DRPLA | hATN1Ex5_36 | CCATCGCTGCCACCACCACCT | 101 | AGGUGGUGGUGGCAGCGAUGG | 102 |
| DRPLA | hATN1Ex5_37 | CCTGCCTCAGGGCCGCCCCTG | 103 | CAGGGGCGGCCCUGAGGCAGG | 104 |
| DRPLA | hATN1Ex5_38 | GCCGGCTGAGGAGTATGAGACC | 105 | GGUCUCAUACUCCUCAGCCGGC | 106 |
| DRPLA | hATN1Ex5_39 | CCAAGGTGGTAGATGTACCCA | 107 | UGGGUACAUCUACCACCUUGG | 108 |
| DRPLA | hATN1Ex5_40 | GCCATGCCAGTCAGTCTGCCAG | 109 | CUGGCAGACUGACUGGCAUGGC | 110 |
| DRPLA | hATN1Ex6_1 | CCTGGATCGCGGCTTCAACTC | 111 | GAGUUGAAGCCGCGAUCCAGG | 112 |
| DRPLA | hATN1Ex6_2 | CCTGTACTTCGTGCCACTGGAGG | 113 | CCUCCAGUGGCACGAAGUACAGG | 114 |
| DRPLA | hATN1Ex6_3 | GACCTGGTGGAGAAGGTGCGGCG | 115 | CGCCGCACCUUCUCCACCAGGUC | 116 |
| DRPLA | hATN1Ex6_4 | CGCGAAGAAAAGGAGCGCGAGCG | 117 | CGCUCGCGCUCCUUUUCUUCGCG | 118 |
| DRPLA | hATN1Ex6_5 | GCGAGCGGGAACGCGAGAAAG | 119 | CUUUCUCGCGUUCCCGCUCGC | 120 |
| DRPLA | hATN1Ex6_6 | GCGAGAAGGAGCGCGAGCTTG | 121 | CAAGCUCGCGCUCCUUCUCGC | 122 |
| SCA3 | hATXN3Ex7_1 | TTGTCGTTAAGGGTGATCTGC | 123 | GCAGAUCACCCUUAACGACAA | 124 |
| SCA3 | hATXN3Ex7_2 | CTGCCAGATTGCGAAGCTGA | 125 | UCAGCUUCGCAAUCUGGCAG | 126 |
| SCA3 | hATXN3Ex7_3 | GACCAACTCCTGCAGATGATT | 127 | AAUCAUCUGCAGGAGUUGGUC | 128 |
| SCA3 | hATXN3Ex7_4 | GGTCCAACAGATGCATCGAC | 129 | GUCGAUGCAUCUGUUGGACC | 130 |
| SCA3 | hATXN3Ex7_5 | GCACAACTAAAAGAGCAAAG | 131 | CUUUGCUCUUUUAGUUGUGC | 132 |
| SCA3 | hATXN3Ex8_1 | GTTAGAAGCAAATGATGGCTC | 133 | GAGCCAUCAUUUGCUUCUAAC | 134 |
| SCA3 | hATXN3Ex8_2 | CTCAGGAATGTTAGACGAAG | 135 | CUUCGUCUAACAUUCCUGAG | 136 |
| SCA3 | hATXN3Ex8_3 | GAGGAGGATTTGCAGAGGGC | 137 | GCCCUCUGCAAAUCCUCCUC | 138 |
| SCA3 | hATXN3Ex8_4 | GAGGAAGCAGATCTCCGCAG | 139 | CUGCGGAGAUCUGCUUCCUC | 140 |
| SCA3 | hATXN3Ex8_5 | GGCTATTCAGCTAAGTATGCAAG | 141 | CUUGCAUACUUAGCUGAAUAGCC | 142 |
| SCA3 | hATXN3Ex9_1 | GGTAGTTCCAGAAACATATCTC | 143 | GAGAUAUGUUUCUGGAACUACC | 144 |
| SCA3 | hATXN3Ex9_2 | GCTTCGGAAGAGACGAGAAGC | 145 | GCUUCUCGUCUCUUCCGAAGC | 146 |
| SCA3 | hATXN3Ex10_1 | CAGCAGCAAAAGCAGCAACAGC | 147 | GCUGUUGCUGCUUUUGCUGCUG | 148 |
| SCA3 | hATXN3Ex10_2 | GACCTATCAGGACAGAGTTC | 149 | GAACUCUGUCCUGAUAGGUC | 150 |
| SCA7 | hATXN7Ex3_1 | GAGCGGAAAGAATGTCGGAGC | 151 | GCUCCGACAUUCUUUCCGCUC | 152 |
| SCA7 | hATXN7Ex3_2 | AGCGGGCCGCGGATGACGTCA | 153 | UGACGUCAUCCGCGGCCCGCU | 154 |
| SCA7 | hATXN7Ex3_3 | AGCAGCCGCCGCCTCCGCAG | 155 | CUGCGGAGGCGGCGGCUGCU | 156 |
| SCA7 | hATXN7Ex3_4 | ACACGGCCGGAGGACGGCG | 157 | CGCCGUCCUCCGGCCGUGU | 158 |
| SCA7 | hATXN7Ex3_5 | GCGCCGCCTCCACCTCGGCCG | 159 | CGGCCGAGGUGGAGGCGGCGC | 160 |
| SCA7 | hATXN7Ex3_6 | ACCTCGGCCGCCGCAATGGCGA | 161 | UCGCCAUUGCGGCGGCCGAGGU | 162 |
| SCA7 | hATXN7Ex3_7 | GGCCTCTGCCCAGTCCTGAAGT | 163 | ACUUCAGGACUGGGCAGAGGCC | 164 |
| SCA7 | hATXN7Ex3_8 | TGATGCTGGGACAGTCGTGGAAT | 165 | AUUCCACGACUGUCCCAGCAUCA | 166 |
| SCA7 | hATXN7Ex3_9 | AGGCTTCCAAACTTCCTGGGAAG | 167 | CUUCCCAGGAAGUUUGGAAGCCU | 168 |
| HD | hHTTEx12_1 | CATCAGCGACAGCTCCCAGACCACCACCG | 169 | CGGUGGUGGUCUGGGAGCUGUCGCUGAUG | 170 |

TABLE 3-continued

AON sequences targeting proteins involved in neurodegenerative diseases

| Disease | AON Name | Target Sequence | SEQ ID NO: | AON Sequence | SEQ ID NO: |
|---|---|---|---|---|---|
| HD | hHTTEx12_2 | TCACAGCACACACTGCAGGC | 171 | GCCUGCAGUGUGUGCUGUGA | 172 |
| HD | hHTTEx12_3 | GGTCAGCAGGTCATGACATCAT | 173 | AUGAUGUCAUGACCUGCUGACC | 174 |
| HD | hHTTEx12_4 | AGAGCTGGCTGCTTCTTCAG | 175 | CUGAAGAAGCAGCCAGCUCU | 176 |
| HD | hHTTEx12_5 | GATGAGGAGGATATCTTGAG | 177 | CUCAAGAUAUCCUCCUCAUC | 178 |
| HD | hHTTEx12_6 | TCAGTGAAGGATGAGATCAGTGG | 179 | CCACUGAUCUCAUCCUUCACUGA | 180 |
| HD | hHTTEx12_7 | ATGGACCTGAATGATGGGAC | 181 | GUCCCAUCAUUCAGGUCCAU | 182 |
| HD | hHTTEx12_8 | TGACAAGCTCTGCCACTGAT | 183 | AUCAGUGGCAGAGCUUGUCA | 184 |
| HD | hHTTEx12_9 | TCCAGCCAGGTCAGCGCCGT | 185 | ACGGCGCUGACCUGGCUGGA | 186 |
| HD | hHTTEx12_10 | ACTCAGTGGATCTGGCCAGCT | 187 | AGCUGGCCAGAUCCACUGAGU | 188 |
| HD | hHTTEx13_1 | CCTGCAGATTGGACAGCC | 189 | GGCUGUCCAAUCUGCAGG | 190 |
| HD | hHTTEx13_2 | GGTACCGACAACCAGTATTT | 191 | AAAUACUGGUUGUCGGUACC | 192 |
| HD | hHTTEx14_1 | AACATGAGTCACTGCAGGCAG | 193 | CUGCCUGCAGUGACUCAUGUU | 194 |
| HD | hHTTEx14_2 | GCCTTCTGACAGCAGTGTTGAT | 195 | AUCAACACUGCUGUCAGAAGGC | 196 |
| HD | hHTTEx14_3 | GTTGAGAGATGAAGCTACTG | 197 | CAGUAGCUUCAUCUCUCAAC | 198 |
| SCA17 | hTBPEx3_1: | GCCATGACTCCCGGAATCCCTA | 199 | UAGGGAUUCCGGGAGUCAUGGC | 200 |
| SCA17 | hTBPEx3_2: | CCTATCTTTAGTCCAATGATGC | 201 | GCAUCAUUGGACUAAAGAUAGG | 202 |
| SCA17 | hTBPEx3_3: | TATGGCACTGGACTGACCCCAC | 203 | GUGGGGUCAGUCCAGUGCCAUA | 204 |
| SCA17 | hTBPEx3_4: | GCAGCTGCAGCCGTTCAGCAG | 205 | CUGCUGAACGGCUGCAGCUGC | 206 |
| SCA17 | hTBPEx3_5: | GTTCAGCAGTCAACGTCCCAGC | 207 | GCUGGGACGUUGACUGCUGAAC | 208 |
| SCA17 | hTBPEx3_6: | AACCTCAGGCCAGGCACCACAG | 209 | CUGUGGUGCCUGGCCUGAGGUU | 210 |
| SCA17 | hTBPEx3_7: | GCACCACAGCTCTTCCACTCA | 211 | UGAGUGGAAGAGCUGUGGUGC | 212 |
| SCA17 | hTBPEx3_8: | CTCACAGACTCTCACAACTGC | 213 | GCAGUUGUGAGAGUCUGUGAG | 214 |
| SCA17 | hTBPEx3_9: | GGCACCACTCCACTGTATCCCT | 215 | AGGGAUACAGUGGAGUGGUGCC | 216 |
| SCA17 | hTBPEx3_10: | CATCACTCCTGCCACGCCAGCT | 217 | AGCUGGCGUGGCAGGAGUGAUG | 218 |
| SCA17 | hTBPEx3_11: | AGAGTTCTGGGATTGTACCGCA | 219 | UGCGGUACAAUCCCAGAACUCU | 220 |
| SCA17 | hTBPEx4_1: | TGTATCCACAGTGAATCTTGGT | 221 | ACCAAGAUUCACUGUGGAUACA | 222 |
| SCA17 | hTBPEx4_2: | GGTTGTAAACTTGACCTAAAG | 223 | CUUUAGGUCAAGUUUACAACC | 224 |
| SCA17 | hTBPEx4_3: | CATTGCACTTCGTGCCCGAAACG | 225 | CGUUUCGGGCACGAAGUGCAAUG | 226 |

The invention claimed is:

1. A method of promoting the production of a human Huntingtin protein lacking a proteolytic caspase-6 cleavage site in a human cell, the method comprising:

providing a human cell that expresses a human Huntingtin protein comprising a caspase-6 proteolytic cleavage site from a pre-mRNA encoding said protein with an anti-sense oligonucleotide that is directed toward the interior of exon 12 of the human Huntingtin gene;

binds to the pre-mRNA to form a double-stranded nucleic acid complex;

induces partial skipping of exon 12, wherein at least nucleotides 207 to 341 of exon 12 are skipped; and wherein each nucleotide of the anti-sense oligonucleotide is chemically modified to render the double-stranded nucleic acid complex RNase H resistant, and allowing translation of mRNA produced from said pre-mRNA in the cell to produce an mRNA lacking nucleotides 207 to 341 of exon 12.

2. The method according to claim 1, wherein the antisense oligonucleotide is a uniformly 2'-O-methoxyethylribose modified phosphorothioate oligonucleotide.

3. A method for treating Huntington's disease in an individual, the method comprising:

administering to an individual in need thereof an anti-sense oligonucleotide directed toward the interior of exon 12 of the human Huntingtin gene that binds to a pre-mRNA produced from the human Huntingtin gene to form a double-stranded nucleic acid complex; and induces partial skipping of exon 12 of the human Huntingtin gene wherein at least nucleotides 207 to 341 of exon 12 are skipped; and wherein each nucleotide of the anti-sense oligonucleotide is chemically modified to render the double-stranded nucleic acid complex RNase H resistant.

4. The method according to claim 3, wherein the antisense oligonucleotide is a uniformly 2'-O-methoxyethylribose modified phosphorothioate oligonucleotide.

5. The method according to claim 1, wherein the antisense nucleotide comprises a sequence according to SEQ ID NO:1.

6. The method according to claim 4, wherein the antisense nucleotide comprises a sequence according to SEQ ID NO:1.

* * * * *

UNITED STATES PATENT AND TRADEMARK OFFICE

CERTIFICATE OF CORRECTION

PATENT NO. : 9,611,471 B2
APPLICATION NO. : 13/814203
DATED : April 4, 2017
INVENTOR(S) : Wilhelmina M. C. van Roon-Mom et al.

It is certified that error appears in the above-identified patent and that said Letters Patent is hereby corrected as shown below:

On the Title Page
In ITEM (73) Assignee: change “Academisch Ziekenhuis Leiden,” to --Academisch Ziekenhuis Leiden h.o.d.n. LUMC,--

Signed and Sealed this
Twenty-eighth Day of January, 2020

Andrei Iancu
*Director of the United States Patent and Trademark Office*

SEQUENCE LISTING

<160> NUMBER OF SEQ ID NOS: 234

<210> SEQ ID NO 1
<211> LENGTH: 29
<212> TYPE: RNA
<213> ORGANISM: Artificial
<220> FEATURE:
<223> OTHER INFORMATION: AON HDEx12_1

<400> SEQUENCE: 1 cgguggugu cugggagcug ucgcugaug 29

<210> SEQ ID NO 2
<211> LENGTH: 19
<212> TYPE: RNA
<213> ORGANISM: Artificial
<220> FEATURE:
<223> OTHER INFORMATION: AON HDEx12_2

<400> SEQUENCE: 2
ucacagcaca cacugcagg 19

<210> SEQ ID NO 3
<211> LENGTH: 28
<212> TYPE: RNA
<213> ORGANISM: Artificial
<220> FEATURE:
<223> OTHER INFORMATION: AON HDEx13_1

<400> SEQUENCE: 3
guuccugaag gccuccgagg cuucauca 28

<210> SEQ ID NO 4
<211> LENGTH: 25
<212> TYPE: RNA
<213> ORGANISM: Artificial
<220> FEATURE:
<223> OTHER INFORMATION: AON HDEx13_2

<400> SEQUENCE: 4
gguccuacuu cuacuccuuc ggugu 25

<210> SEQ ID NO 5
<211> LENGTH: 20
<212> TYPE: RNA
<213> ORGANISM: Artificial
<220> FEATURE:
<223> OTHER INFORMATION: AON DRPLAEx5_18

<400> SEQUENCE: 5
gucgcugcug ccaucaucau 20

<210> SEQ ID NO 6
<211> LENGTH: 20
<212> TYPE: RNA
<213> ORGANISM: Artificial
<220> FEATURE:
<223> OTHER INFORMATION: AON DRPLAEx5_128

<400> SEQUENCE: 6
aagaggaagc aggaggcaga 20

<210> SEQ ID NO 7
<211> LENGTH: 20
<212> TYPE: RNA
<213> ORGANISM: Artificial
<220> FEATURE:
<223> OTHER INFORMATION: AON DRPLAEx5_81

<400> SEQUENCE: 7
ggaggagccu ggaacauucg 20

<210> SEQ ID NO 8
<211> LENGTH: 20
<212> TYPE: RNA

<213> ORGANISM: Artificial
<220> FEATURE:
<223> OTHER INFORMATION: AON DRPLAEx6_80

<400> SEQUENCE: 8
aagcucgcgc uccuucucgc 20

<210> SEQ ID NO 9
<211> LENGTH: 20
<212> TYPE: RNA
<213> ORGANISM: Artificial
<220> FEATURE:
<223> OTHER INFORMATION: AON DRPLAEx6_1

<400> SEQUENCE: 9
cgaguugaag ccgcgaucca 20

<210> SEQ ID NO 10
<211> LENGTH: 20
<212> TYPE: RNA
<213> ORGANISM: Artificial
<220> FEATURE:
<223> OTHER INFORMATION: AON DRPLAEx6_84

<400> SEQUENCE: 10
guucaagcuc gcgcuccuuc 20

<210> SEQ ID NO 11
<211> LENGTH: 23
<212> TYPE: DNA
<213> ORGANISM: Artificial
<220> FEATURE:
<223> OTHER INFORMATION: target hAPPEx15_1

<400> SEQUENCE: 11
gttctgggtt gacaaatatc aag 23

<210> SEQ ID NO 12
<211> LENGTH: 23
<212> TYPE: RNA
<213> ORGANISM: Artificial
<220> FEATURE:
<223> OTHER INFORMATION: AON hAPPEx15_1

<400> SEQUENCE: 12
cuugauauuu gucaacccag aac 23

<210> SEQ ID NO 13
<211> LENGTH: 23
<212> TYPE: DNA
<213> ORGANISM: Artificial
<220> FEATURE:
<223> OTHER INFORMATION: target hAPPEx15_2

<400> SEQUENCE: 13
cggaggagat ctctgaagtg aag 23

<210> SEQ ID NO 14
<211> LENGTH: 23
<212> TYPE: RNA
<213> ORGANISM: Artificial
<220> FEATURE:
<223> OTHER INFORMATION: AON hAPPEx15_2

<400> SEQUENCE: 14
cuucacuuca gagaucuccu ccg 23

<210> SEQ ID NO 15
<211> LENGTH: 21
<212> TYPE: DNA
<213> ORGANISM: Artificial
<220> FEATURE:
<223> OTHER INFORMATION: target hAPPEx15_3

<400> SEQUENCE: 15
gatgcagaat tccgacatga c 21

<210> SEQ ID NO 16
<211> LENGTH: 21
<212> TYPE: RNA
<213> ORGANISM: Artificial
<220> FEATURE:
<223> OTHER INFORMATION: AON hAPPEx15_3

<400> SEQUENCE: 16
gucaugucgg aauucugcau c 21

<210> SEQ ID NO 17
<211> LENGTH: 23
<212> TYPE: DNA
<213> ORGANISM: Artificial
<220> FEATURE:
<223> OTHER INFORMATION: target hAPPEx15_4

<400> SEQUENCE: 17
ctcaggatat gaagttcatc atc 23

<210> SEQ ID NO 18
<211> LENGTH: 23
<212> TYPE: RNA
<213> ORGANISM: Artificial
<220> FEATURE:
<223> OTHER INFORMATION: AON hAPPEx15_4

<400> SEQUENCE: 18
gaugaugaac uucauauccu gag 23

<210> SEQ ID NO 19
<211> LENGTH: 20
<212> TYPE: DNA
<213> ORGANISM: Artificial
<220> FEATURE:
<223> OTHER INFORMATION: target hAPPEx16_1

<400> SEQUENCE: 19
gcaatcattg gactcatggt 20

<210> SEQ ID NO 20
<211> LENGTH: 20
<212> TYPE: RNA
<213> ORGANISM: Artificial
<220> FEATURE:
<223> OTHER INFORMATION: AON hAPPEx16_1

<400> SEQUENCE: 20
accaugaguc caaugauugc 20

<210> SEQ ID NO 21
<211> LENGTH: 20
<212> TYPE: DNA
<213> ORGANISM: Artificial
<220> FEATURE:

<223> OTHER INFORMATION: target hAPPEx16_2

<400> SEQUENCE: 21
gatcgtcatc accttggtga 20

<210> SEQ ID NO 22
<211> LENGTH: 20
<212> TYPE: RNA
<213> ORGANISM: Artificial
<220> FEATURE:
<223> OTHER INFORMATION: AON hAPPEx16_2

<400> SEQUENCE: 22
ucaccaaggu gaugacgauc 20

<210> SEQ ID NO 23
<211> LENGTH: 23
<212> TYPE: DNA
<213> ORGANISM: Artificial
<220> FEATURE:
<223> OTHER INFORMATION: target hAPPEx16_3

<400> SEQUENCE: 23
gtacacatcc attcatcatg gtg 23

<210> SEQ ID NO 24
<211> LENGTH: 23
<212> TYPE: RNA
<213> ORGANISM: Artificial
<220> FEATURE:
<223> OTHER INFORMATION: AON hAPPEx16_3

<400> SEQUENCE: 24
caccaugaug aauggaugug uac 23

<210> SEQ ID NO 25
<211> LENGTH: 21
<212> TYPE: DNA
<213> ORGANISM: Artificial
<220> FEATURE:
<223> OTHER INFORMATION: target hAPPEx16_4

<400> SEQUENCE: 25
gcagaagatg tgggttcaaa c 21

<210> SEQ ID NO 26
<211> LENGTH: 21
<212> TYPE: RNA
<213> ORGANISM: Artificial
<220> FEATURE:
<223> OTHER INFORMATION: AON hAPPEx16_4

<400> SEQUENCE: 26
guuugaaccc acaucuucug c 21

<210> SEQ ID NO 27
<211> LENGTH: 22
<212> TYPE: DNA
<213> ORGANISM: Artificial
<220> FEATURE:
<223> OTHER INFORMATION: target hAPPEx16_5

<400> SEQUENCE: 27
ggtgatgctg aagaagaaac ag 22

<210> SEQ ID NO 28
<211> LENGTH: 22
<212> TYPE: RNA
<213> ORGANISM: Artificial
<220> FEATURE:
<223> OTHER INFORMATION: AON hAPPEx16_5

<400> SEQUENCE: 28
cuguuucuuc uucagcauca cc 22

<210> SEQ ID NO 29
<211> LENGTH: 23
<212> TYPE: DNA
<213> ORGANISM: Artificial
<220> FEATURE:
<223> OTHER INFORMATION: target hAPPEx16_6

<400> SEQUENCE: 29
tcatcatggt gtggtggagg tag 23

<210> SEQ ID NO 30
<211> LENGTH: 23
<212> TYPE: RNA
<213> ORGANISM: Artificial
<220> FEATURE:
<223> OTHER INFORMATION: AON hAPPEx16_6

<400> SEQUENCE: 30
cuaccuccac cacaccauga uga 23

<210> SEQ ID NO 31
<211> LENGTH: 22
<212> TYPE: DNA
<213> ORGANISM: Artificial
<220> FEATURE:
<223> OTHER INFORMATION: target hATN1Ex5_1

<400> SEQUENCE: 31
ctccctcggc cacagtctcc ct 22

<210> SEQ ID NO 32
<211> LENGTH: 22
<212> TYPE: RNA
<213> ORGANISM: Artificial
<220> FEATURE:
<223> OTHER INFORMATION: AON hATN1Ex5_1

<400> SEQUENCE: 32
agggagacug uggccgaggg ag 22

<210> SEQ ID NO 33
<211> LENGTH: 22
<212> TYPE: DNA
<213> ORGANISM: Artificial
<220> FEATURE:
<223> OTHER INFORMATION: target hATN1Ex5_2

<400> SEQUENCE: 33
gcggagcctt aatgatgatg gc 22

<210> SEQ ID NO 34
<211> LENGTH: 22
<212> TYPE: RNA
<213> ORGANISM: Artificial
<220> FEATURE:
<223> OTHER INFORMATION: AON hATN1Ex5_2

<400> SEQUENCE: 34
gccaucauca uuaaggcucc gc 22

<210> SEQ ID NO 35
<211> LENGTH: 22
<212> TYPE: DNA
<213> ORGANISM: Artificial
<220> FEATURE:
<223> OTHER INFORMATION: target hATN1Ex5_3

<400> SEQUENCE: 35
agcagcgacc ctagggatat cg 22

<210> SEQ ID NO 36
<211> LENGTH: 22
<212> TYPE: RNA
<213> ORGANISM: Artificial
<220> FEATURE:
<223> OTHER INFORMATION: AON hATN1Ex5_3

<400> SEQUENCE: 36
cgauaucccu agggucgcug cu 22

<210> SEQ ID NO 37
<211> LENGTH: 21
<212> TYPE: DNA
<213> ORGANISM: Artificial
<220> FEATURE:
<223> OTHER INFORMATION: target hATN1Ex5_4

<400> SEQUENCE: 37
aggacaaccg aagcacgtcc c 21

<210> SEQ ID NO 38
<211> LENGTH: 21
<212> TYPE: RNA
<213> ORGANISM: Artificial
<220> FEATURE:
<223> OTHER INFORMATION: AON hATN1Ex5_4

<400> SEQUENCE: 38
gggacgugcu ucgguugucc u 21

<210> SEQ ID NO 39
<211> LENGTH: 23
<212> TYPE: DNA
<213> ORGANISM: Artificial
<220> FEATURE:
<223> OTHER INFORMATION: target hATN1Ex5_5

<400> SEQUENCE: 39
tggaagtgtg gagaatgact ctg 23

<210> SEQ ID NO 40
<211> LENGTH: 23
<212> TYPE: RNA
<213> ORGANISM: Artificial
<220> FEATURE:
<223> OTHER INFORMATION: AON hATN1Ex5_5

<400> SEQUENCE: 40
cagagucauu cuccacacuu cca 23

<210> SEQ ID NO 41
<211> LENGTH: 22

<212> TYPE: DNA
<213> ORGANISM: Artificial
<220> FEATURE:
<223> OTHER INFORMATION: target hATN1Ex5_6

<400> SEQUENCE: 41
atcttctggc ctgtcccagg gc 22

<210> SEQ ID NO 42
<211> LENGTH: 22
<212> TYPE: RNA
<213> ORGANISM: Artificial
<220> FEATURE:
<223> OTHER INFORMATION: AON hATN1Ex5_6

<400> SEQUENCE: 42
gcccugggac aggccagaag au 22

<210> SEQ ID NO 43
<211> LENGTH: 23
<212> TYPE: DNA
<213> ORGANISM: Artificial
<220> FEATURE:
<223> OTHER INFORMATION: target hATN1Ex5_7

<400> SEQUENCE: 43
cgacagccag aggctagctt tga 23

<210> SEQ ID NO 44
<211> LENGTH: 23
<212> TYPE: RNA
<213> ORGANISM: Artificial
<220> FEATURE:
<223> OTHER INFORMATION: AON hATN1Ex5_7

<400> SEQUENCE: 44
ucaaagcuag ccucuggcug ucg 23

<210> SEQ ID NO 45
<211> LENGTH: 22
<212> TYPE: DNA
<213> ORGANISM: Artificial
<220> FEATURE:
<223> OTHER INFORMATION: target hATN1Ex5_8

<400> SEQUENCE: 45
ctcgaatgtt ccaggctcct cc 22

<210> SEQ ID NO 46
<211> LENGTH: 22
<212> TYPE: RNA
<213> ORGANISM: Artificial
<220> FEATURE:
<223> OTHER INFORMATION: AON hATN1Ex5_8

<400> SEQUENCE: 46
ggaggagccu ggaacauucg ag 22

<210> SEQ ID NO 47
<211> LENGTH: 22
<212> TYPE: DNA
<213> ORGANISM: Artificial
<220> FEATURE:
<223> OTHER INFORMATION: target hATN1Ex5_9

<400> SEQUENCE: 47

```
tctatcctgg gggcactggt gg                                                22


<210> SEQ ID NO 48
<211> LENGTH: 22
<212> TYPE: RNA
<213> ORGANISM: Artificial
<220> FEATURE:
<223> OTHER INFORMATION: AON hATN1Ex5_9

<400> SEQUENCE: 48

ccaccagugc ccccaggaua ga                                                22


<210> SEQ ID NO 49
<211> LENGTH: 22
<212> TYPE: DNA
<213> ORGANISM: Artificial
<220> FEATURE:
<223> OTHER INFORMATION: target hATN1Ex5_10

<400> SEQUENCE: 49

tggaccccca atgggtccca ag                                                22


<210> SEQ ID NO 50
<211> LENGTH: 22
<212> TYPE: RNA
<213> ORGANISM: Artificial
<220> FEATURE:
<223> OTHER INFORMATION: AON hATN1Ex5_10

<400> SEQUENCE: 50

cuugggaccc auugggggu c ca                                               22


<210> SEQ ID NO 51
<211> LENGTH: 20
<212> TYPE: DNA
<213> ORGANISM: Artificial
<220> FEATURE:
<223> OTHER INFORMATION: target hATN1Ex5_11

<400> SEQUENCE: 51

aggggctgcc tcatcagtgg                                                   20


<210> SEQ ID NO 52
<211> LENGTH: 20
<212> TYPE: RNA
<213> ORGANISM: Artificial
<220> FEATURE:
<223> OTHER INFORMATION: AON hATN1Ex5_11

<400> SEQUENCE: 52

ccacugauga ggcagccccu                                                   20


<210> SEQ ID NO 53
<211> LENGTH: 23
<212> TYPE: DNA
<213> ORGANISM: Artificial
<220> FEATURE:
<223> OTHER INFORMATION: target hATN1Ex5_12

<400> SEQUENCE: 53

aagctctggg gctagtggtg ctc                                               23


<210> SEQ ID NO 54
<211> LENGTH: 23
<212> TYPE: RNA
<213> ORGANISM: Artificial
```

<220> FEATURE:
<223> OTHER INFORMATION: AON hATN1Ex5_12

<400> SEQUENCE: 54
gagcaccacu agccccagag cuu 23

<210> SEQ ID NO 55
<211> LENGTH: 22
<212> TYPE: DNA
<213> ORGANISM: Artificial
<220> FEATURE:
<223> OTHER INFORMATION: target hATN1Ex5_13

<400> SEQUENCE: 55
acaaagccgc ctaccactcc ag 22

<210> SEQ ID NO 56
<211> LENGTH: 22
<212> TYPE: RNA
<213> ORGANISM: Artificial
<220> FEATURE:
<223> OTHER INFORMATION: AON hATN1Ex5_13

<400> SEQUENCE: 56
cuggaguggu aggcggcuuu gu 22

<210> SEQ ID NO 57
<211> LENGTH: 21
<212> TYPE: DNA
<213> ORGANISM: Artificial
<220> FEATURE:
<223> OTHER INFORMATION: target hATN1Ex5_14

<400> SEQUENCE: 57
ctccaccacc agccaacttc c 21

<210> SEQ ID NO 58
<211> LENGTH: 21
<212> TYPE: RNA
<213> ORGANISM: Artificial
<220> FEATURE:
<223> OTHER INFORMATION: AON hATN1Ex5_14

<400> SEQUENCE: 58
ggaaguuggc ugguggugga g 21

<210> SEQ ID NO 59
<211> LENGTH: 22
<212> TYPE: DNA
<213> ORGANISM: Artificial
<220> FEATURE:
<223> OTHER INFORMATION: target hATN1Ex5_15

<400> SEQUENCE: 59
ccaaccacta cctggtcatc tg 22

<210> SEQ ID NO 60
<211> LENGTH: 22
<212> TYPE: RNA
<213> ORGANISM: Artificial
<220> FEATURE:
<223> OTHER INFORMATION: AON hATN1Ex5_15

<400> SEQUENCE: 60
cagaugacca gguagugguu gg 22

<210> SEQ ID NO 61
<211> LENGTH: 21
<212> TYPE: DNA
<213> ORGANISM: Artificial
<220> FEATURE:
<223> OTHER INFORMATION: target hATN1Ex5_16

<400> SEQUENCE: 61
tggcccagag aagggcccaa c 21

<210> SEQ ID NO 62
<211> LENGTH: 21
<212> TYPE: RNA
<213> ORGANISM: Artificial
<220> FEATURE:
<223> OTHER INFORMATION: AON hATN1Ex5_16

<400> SEQUENCE: 62
guugggcccu ucucugggcc a 21

<210> SEQ ID NO 63
<211> LENGTH: 21
<212> TYPE: DNA
<213> ORGANISM: Artificial
<220> FEATURE:
<223> OTHER INFORMATION: target hATN1Ex5_17

<400> SEQUENCE: 63
ttcctcttct gctccagcgc c 21

<210> SEQ ID NO 64
<211> LENGTH: 21
<212> TYPE: RNA
<213> ORGANISM: Artificial
<220> FEATURE:
<223> OTHER INFORMATION: AON hATN1Ex5_17

<400> SEQUENCE: 64
ggcgcuggag cagaagagga a 21

<210> SEQ ID NO 65
<211> LENGTH: 21
<212> TYPE: DNA
<213> ORGANISM: Artificial
<220> FEATURE:
<223> OTHER INFORMATION: target hATN1Ex5_18

<400> SEQUENCE: 65
gtttccttat tcatcctcta g 21

<210> SEQ ID NO 66
<211> LENGTH: 21
<212> TYPE: RNA
<213> ORGANISM: Artificial
<220> FEATURE:
<223> OTHER INFORMATION: AON hATN1Ex5_18

<400> SEQUENCE: 66
cuagaggaug aauaaggaaa c 21

<210> SEQ ID NO 67
<211> LENGTH: 21
<212> TYPE: DNA
<213> ORGANISM: Artificial
<220> FEATURE:
<223> OTHER INFORMATION: target hATN1Ex5_19

<400> SEQUENCE: 67
gcctctctgt ctccaatcag c 21

<210> SEQ ID NO 68
<211> LENGTH: 21
<212> TYPE: RNA
<213> ORGANISM: Artificial
<220> FEATURE:
<223> OTHER INFORMATION: AON hATN1Ex5_19

<400> SEQUENCE: 68
gcugauugga gacagagagg c 21

<210> SEQ ID NO 69
<211> LENGTH: 20
<212> TYPE: DNA
<213> ORGANISM: Artificial
<220> FEATURE:
<223> OTHER INFORMATION: target hATN1Ex5_20

<400> SEQUENCE: 69
ccatcccagg ctgtgtggag 20

<210> SEQ ID NO 70
<211> LENGTH: 20
<212> TYPE: RNA
<213> ORGANISM: Artificial
<220> FEATURE:
<223> OTHER INFORMATION: AON hATN1Ex5_20

<400> SEQUENCE: 70
cuccacacag ccugggaugg 20

<210> SEQ ID NO 71
<211> LENGTH: 22
<212> TYPE: DNA
<213> ORGANISM: Artificial
<220> FEATURE:
<223> OTHER INFORMATION: target hATN1Ex5_21

<400> SEQUENCE: 71
tctactgggg cccagtccac cg 22

<210> SEQ ID NO 72
<211> LENGTH: 22
<212> TYPE: RNA
<213> ORGANISM: Artificial
<220> FEATURE:
<223> OTHER INFORMATION: AON hATN1Ex5_21

<400> SEQUENCE: 72
cgguggacug ggccccagua ga 22

<210> SEQ ID NO 73
<211> LENGTH: 21
<212> TYPE: DNA
<213> ORGANISM: Artificial
<220> FEATURE:
<223> OTHER INFORMATION: target hATN1Ex5_22

<400> SEQUENCE: 73
gcatcacgga aactctgggc c 21

<210> SEQ ID NO 74

<211> LENGTH: 21
<212> TYPE: RNA
<213> ORGANISM: Artificial
<220> FEATURE:
<223> OTHER INFORMATION: AON hATN1Ex5_22

<400> SEQUENCE: 74
ggcccagagu uuccgugaug c 21

<210> SEQ ID NO 75
<211> LENGTH: 21
<212> TYPE: DNA
<213> ORGANISM: Artificial
<220> FEATURE:
<223> OTHER INFORMATION: target hATN1Ex5_23

<400> SEQUENCE: 75
ccactggagg gcggtagctc c 21

<210> SEQ ID NO 76
<211> LENGTH: 21
<212> TYPE: RNA
<213> ORGANISM: Artificial
<220> FEATURE:
<223> OTHER INFORMATION: AON hATN1Ex5_23

<400> SEQUENCE: 76
ggagcuaccg cccuccagug g 21

<210> SEQ ID NO 77
<211> LENGTH: 21
<212> TYPE: DNA
<213> ORGANISM: Artificial
<220> FEATURE:
<223> OTHER INFORMATION: target hATN1Ex5_24

<400> SEQUENCE: 77
ctccctgggg tctctgaggc c 21

<210> SEQ ID NO 78
<211> LENGTH: 21
<212> TYPE: RNA
<213> ORGANISM: Artificial
<220> FEATURE:
<223> OTHER INFORMATION: AON hATN1Ex5_24

<400> SEQUENCE: 78
ggccucagag accccaggga g 21

<210> SEQ ID NO 79
<211> LENGTH: 21
<212> TYPE: DNA
<213> ORGANISM: Artificial
<220> FEATURE:
<223> OTHER INFORMATION: target hATN1Ex5_25

<400> SEQUENCE: 79
caccagggcc agcacacctg c 21

<210> SEQ ID NO 80
<211> LENGTH: 21
<212> TYPE: RNA
<213> ORGANISM: Artificial
<220> FEATURE:
<223> OTHER INFORMATION: AON hATN1Ex5_25

<400> SEQUENCE: 80
gcaggugugc uggcccuggu g 21

<210> SEQ ID NO 81
<211> LENGTH: 22
<212> TYPE: DNA
<213> ORGANISM: Artificial
<220> FEATURE:
<223> OTHER INFORMATION: target hATN1Ex5_26

<400> SEQUENCE: 81
gtgtcctaca gccaagcagg cc 22

<210> SEQ ID NO 82
<211> LENGTH: 22
<212> TYPE: RNA
<213> ORGANISM: Artificial
<220> FEATURE:
<223> OTHER INFORMATION: AON hATN1Ex5_26

<400> SEQUENCE: 82
ggccugcuug gcuguaggac ac 22

<210> SEQ ID NO 83
<211> LENGTH: 22
<212> TYPE: DNA
<213> ORGANISM: Artificial
<220> FEATURE:
<223> OTHER INFORMATION: target hATN1Ex5_27

<400> SEQUENCE: 83
caagggtcct acccatgttc ac 22

<210> SEQ ID NO 84
<211> LENGTH: 22
<212> TYPE: RNA
<213> ORGANISM: Artificial
<220> FEATURE:
<223> OTHER INFORMATION: AON hATN1Ex5_27

<400> SEQUENCE: 84
gugaacaugg guaggacccu ug 22

<210> SEQ ID NO 85
<211> LENGTH: 22
<212> TYPE: DNA
<213> ORGANISM: Artificial
<220> FEATURE:
<223> OTHER INFORMATION: target hATN1Ex5_28

<400> SEQUENCE: 85
caccggtgcc tacggtcacc ac 22

<210> SEQ ID NO 86
<211> LENGTH: 22
<212> TYPE: RNA
<213> ORGANISM: Artificial
<220> FEATURE:
<223> OTHER INFORMATION: AON hATN1Ex5_28

<400> SEQUENCE: 86
guggugaccg uaggcaccgg ug 22

<210> SEQ ID NO 87
<211> LENGTH: 21
<212> TYPE: DNA

<213> ORGANISM: Artificial
<220> FEATURE:
<223> OTHER INFORMATION: target hATN1Ex5_29

<400> SEQUENCE: 87
ctcttcggct accctttcca c 21

<210> SEQ ID NO 88
<211> LENGTH: 21
<212> TYPE: RNA
<213> ORGANISM: Artificial
<220> FEATURE:
<223> OTHER INFORMATION: AON hATN1Ex5_29

<400> SEQUENCE: 88
guggaaaggg uagccgaaga g 21

<210> SEQ ID NO 89
<211> LENGTH: 21
<212> TYPE: DNA
<213> ORGANISM: Artificial
<220> FEATURE:
<223> OTHER INFORMATION: target hATN1Ex5_30

<400> SEQUENCE: 89
ggtcattgcc accgtggctt c 21

<210> SEQ ID NO 90
<211> LENGTH: 21
<212> TYPE: RNA
<213> ORGANISM: Artificial
<220> FEATURE:
<223> OTHER INFORMATION: AON hATN1Ex5_30

<400> SEQUENCE: 90
gaagccacgg uggcaaugac c 21

<210> SEQ ID NO 91
<211> LENGTH: 21
<212> TYPE: DNA
<213> ORGANISM: Artificial
<220> FEATURE:
<223> OTHER INFORMATION: target hATN1Ex5_31

<400> SEQUENCE: 91
ccaccgtacg gaaagagagc c 21

<210> SEQ ID NO 92
<211> LENGTH: 21
<212> TYPE: RNA
<213> ORGANISM: Artificial
<220> FEATURE:
<223> OTHER INFORMATION: AON hATN1Ex5_31

<400> SEQUENCE: 92
ggcucucuuu ccguacggug g 21

<210> SEQ ID NO 93
<211> LENGTH: 23
<212> TYPE: DNA
<213> ORGANISM: Artificial
<220> FEATURE:
<223> OTHER INFORMATION: target hATN1Ex5_32

<400> SEQUENCE: 93
ccaccgggct atcgaggaac ctc 23

<210> SEQ ID NO 94
<211> LENGTH: 23
<212> TYPE: RNA
<213> ORGANISM: Artificial
<220> FEATURE:
<223> OTHER INFORMATION: AON hATN1Ex5_32

<400> SEQUENCE: 94
gagguuccuc gauagcccgg ugg 23

<210> SEQ ID NO 95
<211> LENGTH: 22
<212> TYPE: DNA
<213> ORGANISM: Artificial
<220> FEATURE:
<223> OTHER INFORMATION: target hATN1Ex5_33

<400> SEQUENCE: 95
caggcccagg gaccttcaag cc 22

<210> SEQ ID NO 96
<211> LENGTH: 22
<212> TYPE: RNA
<213> ORGANISM: Artificial
<220> FEATURE:
<223> OTHER INFORMATION: AON hATN1Ex5_33

<400> SEQUENCE: 96
ggcuugaagg ucccugggcc ug 22

<210> SEQ ID NO 97
<211> LENGTH: 23
<212> TYPE: DNA
<213> ORGANISM: Artificial
<220> FEATURE:
<223> OTHER INFORMATION: target hATN1Ex5_34

<400> SEQUENCE: 97
ccaccgtggg acctgggccc ctg 23

<210> SEQ ID NO 98
<211> LENGTH: 23
<212> TYPE: RNA
<213> ORGANISM: Artificial
<220> FEATURE:
<223> OTHER INFORMATION: AON hATN1Ex5_34

<400> SEQUENCE: 98
caggggccca ggucccacgg ugg 23

<210> SEQ ID NO 99
<211> LENGTH: 22
<212> TYPE: DNA
<213> ORGANISM: Artificial
<220> FEATURE:
<223> OTHER INFORMATION: target hATN1Ex5_35

<400> SEQUENCE: 99
gccacctgcg gggccctcag gc 22

<210> SEQ ID NO 100
<211> LENGTH: 22
<212> TYPE: RNA
<213> ORGANISM: Artificial
<220> FEATURE:

<223> OTHER INFORMATION: AON hATN1Ex5_35

<400> SEQUENCE: 100
gccugagggc cccgcaggug gc 22

<210> SEQ ID NO 101
<211> LENGTH: 21
<212> TYPE: DNA
<213> ORGANISM: Artificial
<220> FEATURE:
<223> OTHER INFORMATION: target hATN1Ex5_36

<400> SEQUENCE: 101
ccatcgctgc caccaccacc t 21

<210> SEQ ID NO 102
<211> LENGTH: 21
<212> TYPE: RNA
<213> ORGANISM: Artificial
<220> FEATURE:
<223> OTHER INFORMATION: AON hATN1Ex5_36

<400> SEQUENCE: 102
aggugguggu ggcagcgaug g 21

<210> SEQ ID NO 103
<211> LENGTH: 21
<212> TYPE: DNA
<213> ORGANISM: Artificial
<220> FEATURE:
<223> OTHER INFORMATION: target hATN1Ex5_37

<400> SEQUENCE: 103
cctgcctcag ggccgcccct g 21

<210> SEQ ID NO 104
<211> LENGTH: 21
<212> TYPE: RNA
<213> ORGANISM: Artificial
<220> FEATURE:
<223> OTHER INFORMATION: AON hATN1Ex5_37

<400> SEQUENCE: 104
caggggcggc ccugaggcag g 21

<210> SEQ ID NO 105
<211> LENGTH: 22
<212> TYPE: DNA
<213> ORGANISM: Artificial
<220> FEATURE:
<223> OTHER INFORMATION: target hATN1Ex5_38

<400> SEQUENCE: 105
gccggctgag gagtatgaga cc 22

<210> SEQ ID NO 106
<211> LENGTH: 22
<212> TYPE: RNA
<213> ORGANISM: Artificial
<220> FEATURE:
<223> OTHER INFORMATION: AON hATN1Ex5_38

<400> SEQUENCE: 106
ggucucauac uccucagccg gc 22

<210> SEQ ID NO 107
<211> LENGTH: 21
<212> TYPE: DNA
<213> ORGANISM: Artificial
<220> FEATURE:
<223> OTHER INFORMATION: target hATN1Ex5_39

<400> SEQUENCE: 107
ccaaggtggt agatgtaccc a 21

<210> SEQ ID NO 108
<211> LENGTH: 21
<212> TYPE: RNA
<213> ORGANISM: Artificial
<220> FEATURE:
<223> OTHER INFORMATION: AON hATN1Ex5_

<400> SEQUENCE: 108
uggguacauc uaccaccuug g 21

<210> SEQ ID NO 109
<211> LENGTH: 22
<212> TYPE: DNA
<213> ORGANISM: Artificial
<220> FEATURE:
<223> OTHER INFORMATION: target hATN1Ex5_40

<400> SEQUENCE: 109
gccatgccag tcagtctgcc ag 22

<210> SEQ ID NO 110
<211> LENGTH: 22
<212> TYPE: RNA
<213> ORGANISM: Artificial
<220> FEATURE:
<223> OTHER INFORMATION: AON hATN1Ex5_40

<400> SEQUENCE: 110
cuggcagacu gacuggcaug gc 22

<210> SEQ ID NO 111
<211> LENGTH: 21
<212> TYPE: DNA
<213> ORGANISM: Artificial
<220> FEATURE:
<223> OTHER INFORMATION: target hATN1Ex6_1

<400> SEQUENCE: 111
cctggatcgc ggcttcaact c 21

<210> SEQ ID NO 112
<211> LENGTH: 21
<212> TYPE: RNA
<213> ORGANISM: Artificial
<220> FEATURE:
<223> OTHER INFORMATION: AON hATN1Ex6_1

<400> SEQUENCE: 112
gaguugaagc cgcgauccag g 21

<210> SEQ ID NO 113
<211> LENGTH: 23
<212> TYPE: DNA
<213> ORGANISM: Artificial
<220> FEATURE:
<223> OTHER INFORMATION: target hATN1Ex6_2

<400> SEQUENCE: 113
cctgtacttc gtgccactgg agg 23

<210> SEQ ID NO 114
<211> LENGTH: 23
<212> TYPE: RNA
<213> ORGANISM: Artificial
<220> FEATURE:
<223> OTHER INFORMATION: AON hATN1Ex6_2

<400> SEQUENCE: 114
ccuccagugg cacgaaguac agg 23

<210> SEQ ID NO 115
<211> LENGTH: 23
<212> TYPE: DNA
<213> ORGANISM: Artificial
<220> FEATURE:
<223> OTHER INFORMATION: target hATN1Ex6_3

<400> SEQUENCE: 115
gacctggtgg agaaggtgcg gcg 23

<210> SEQ ID NO 116
<211> LENGTH: 23
<212> TYPE: RNA
<213> ORGANISM: Artificial
<220> FEATURE:
<223> OTHER INFORMATION: AON hATN1Ex6_3

<400> SEQUENCE: 116
cgccgcaccu ucuccaccag guc 23

<210> SEQ ID NO 117
<211> LENGTH: 23
<212> TYPE: DNA
<213> ORGANISM: Artificial
<220> FEATURE:
<223> OTHER INFORMATION: target hATN1Ex6_4

<400> SEQUENCE: 117
cgcgaagaaa aggagcgcga gcg 23

<210> SEQ ID NO 118
<211> LENGTH: 23
<212> TYPE: RNA
<213> ORGANISM: Artificial
<220> FEATURE:
<223> OTHER INFORMATION: AON hATN1Ex6_4

<400> SEQUENCE: 118
cgcucgcgcu ccuuuucuuc gcg 23

<210> SEQ ID NO 119
<211> LENGTH: 21
<212> TYPE: DNA
<213> ORGANISM: Artificial
<220> FEATURE:
<223> OTHER INFORMATION: target hATN1Ex6_5

<400> SEQUENCE: 119
gcgagcggga acgcgagaaa g 21

<210> SEQ ID NO 120
<211> LENGTH: 21

<212> TYPE: RNA
<213> ORGANISM: Artificial
<220> FEATURE:
<223> OTHER INFORMATION: AON hATN1Ex6_5

<400> SEQUENCE: 120
cuuucucgcg uucccgcucg c 21

<210> SEQ ID NO 121
<211> LENGTH: 21
<212> TYPE: DNA
<213> ORGANISM: Artificial
<220> FEATURE:
<223> OTHER INFORMATION: target hATN1Ex6_6

<400> SEQUENCE: 121
gcgagaagga gcgcgagctt g 21

<210> SEQ ID NO 122
<211> LENGTH: 21
<212> TYPE: RNA
<213> ORGANISM: Artificial
<220> FEATURE:
<223> OTHER INFORMATION: AON hATN1Ex6_6

<400> SEQUENCE: 122
caagcucgcg cuccuucucg c 21

<210> SEQ ID NO 123
<211> LENGTH: 21
<212> TYPE: DNA
<213> ORGANISM: Artificial
<220> FEATURE:
<223> OTHER INFORMATION: target hATXN3Ex7_1

<400> SEQUENCE: 123
ttgtcgttaa gggtgatctg c 21

<210> SEQ ID NO 124
<211> LENGTH: 21
<212> TYPE: RNA
<213> ORGANISM: Artificial
<220> FEATURE:
<223> OTHER INFORMATION: AON hATXN3Ex7_1

<400> SEQUENCE: 124
gcagaucacc cuuaacgaca a 21

<210> SEQ ID NO 125
<211> LENGTH: 20
<212> TYPE: DNA
<213> ORGANISM: Artificial
<220> FEATURE:
<223> OTHER INFORMATION: target hATXN3Ex7_2

<400> SEQUENCE: 125
ctgccagatt gcgaagctga 20

<210> SEQ ID NO 126
<211> LENGTH: 20
<212> TYPE: RNA
<213> ORGANISM: Artificial
<220> FEATURE:
<223> OTHER INFORMATION: AON hATXN3Ex7_2

<400> SEQUENCE: 126
ucagcuucgc aaucuggcag 20

<210> SEQ ID NO 127
<211> LENGTH: 21
<212> TYPE: DNA
<213> ORGANISM: Artificial
<220> FEATURE:
<223> OTHER INFORMATION: target hATXN3Ex7_3

<400> SEQUENCE: 127
gaccaactcc tgcagatgat t 21

<210> SEQ ID NO 128
<211> LENGTH: 21
<212> TYPE: RNA
<213> ORGANISM: Artificial
<220> FEATURE:
<223> OTHER INFORMATION: AON hATXN3Ex7_3

<400> SEQUENCE: 128
aaucaucugc aggaguuggu c 21

<210> SEQ ID NO 129
<211> LENGTH: 20
<212> TYPE: DNA
<213> ORGANISM: Artificial
<220> FEATURE:
<223> OTHER INFORMATION: target hATXN3Ex7_4

<400> SEQUENCE: 129
ggtccaacag atgcatcgac 20

<210> SEQ ID NO 130
<211> LENGTH: 20
<212> TYPE: RNA
<213> ORGANISM: Artificial
<220> FEATURE:
<223> OTHER INFORMATION: AON hATXN3Ex7_4

<400> SEQUENCE: 130
gucgaugcau cuguuggacc 20

<210> SEQ ID NO 131
<211> LENGTH: 20
<212> TYPE: DNA
<213> ORGANISM: Artificial
<220> FEATURE:
<223> OTHER INFORMATION: target hATXN3Ex7_5

<400> SEQUENCE: 131
gcacaactaa aagagcaaag 20

<210> SEQ ID NO 132
<211> LENGTH: 20
<212> TYPE: RNA
<213> ORGANISM: Artificial
<220> FEATURE:
<223> OTHER INFORMATION: AON hATXN3Ex7_5

<400> SEQUENCE: 132
cuuugcucuu uuaguugugc 20

<210> SEQ ID NO 133
<211> LENGTH: 21
<212> TYPE: DNA
<213> ORGANISM: Artificial

<220> FEATURE:
<223> OTHER INFORMATION: target hATXN3Ex8_1

<400> SEQUENCE: 133
gttagaagca aatgatggct c 21

<210> SEQ ID NO 134
<211> LENGTH: 21
<212> TYPE: RNA
<213> ORGANISM: Artificial
<220> FEATURE:
<223> OTHER INFORMATION: AON hATXN3Ex8_1

<400> SEQUENCE: 134
gagccaucau uugcuucuaa c 21

<210> SEQ ID NO 135
<211> LENGTH: 20
<212> TYPE: DNA
<213> ORGANISM: Artificial
<220> FEATURE:
<223> OTHER INFORMATION: target hATXN3Ex8_2

<400> SEQUENCE: 135
ctcaggaatg ttagacgaag 20

<210> SEQ ID NO 136
<211> LENGTH: 20
<212> TYPE: RNA
<213> ORGANISM: Artificial
<220> FEATURE:
<223> OTHER INFORMATION: AON hATXN3Ex8_2

<400> SEQUENCE: 136
cuucgucuaa cauuccugag 20

<210> SEQ ID NO 137
<211> LENGTH: 20
<212> TYPE: DNA
<213> ORGANISM: Artificial
<220> FEATURE:
<223> OTHER INFORMATION: target hATXN3Ex8_3

<400> SEQUENCE: 137
gaggaggatt tgcagagggc 20

<210> SEQ ID NO 138
<211> LENGTH: 20
<212> TYPE: RNA
<213> ORGANISM: Artificial
<220> FEATURE:
<223> OTHER INFORMATION: AON hATXN3Ex8_3

<400> SEQUENCE: 138
gcccucugca aauccuccuc 20

<210> SEQ ID NO 139
<211> LENGTH: 20
<212> TYPE: DNA
<213> ORGANISM: Artificial
<220> FEATURE:
<223> OTHER INFORMATION: target hATXN3Ex8_4

<400> SEQUENCE: 139
gaggaagcag atctccgcag 20

<210> SEQ ID NO 140
<211> LENGTH: 20
<212> TYPE: RNA
<213> ORGANISM: Artificial
<220> FEATURE:
<223> OTHER INFORMATION: AON hATXN3Ex8_4

<400> SEQUENCE: 140
cugcggagau cugcuuccuc 20

<210> SEQ ID NO 141
<211> LENGTH: 23
<212> TYPE: DNA
<213> ORGANISM: Artificial
<220> FEATURE:
<223> OTHER INFORMATION: target hATXN3Ex8_5

<400> SEQUENCE: 141
ggctattcag ctaagtatgc aag 23

<210> SEQ ID NO 142
<211> LENGTH: 23
<212> TYPE: RNA
<213> ORGANISM: Artificial
<220> FEATURE:
<223> OTHER INFORMATION: AON hATXN3Ex8_5

<400> SEQUENCE: 142
cuugcauacu uagcugaaua gcc 23

<210> SEQ ID NO 143
<211> LENGTH: 22
<212> TYPE: DNA
<213> ORGANISM: Artificial
<220> FEATURE:
<223> OTHER INFORMATION: target hATXN3Ex9_1

<400> SEQUENCE: 143
ggtagttcca gaaacatatc tc 22

<210> SEQ ID NO 144
<211> LENGTH: 22
<212> TYPE: RNA
<213> ORGANISM: Artificial
<220> FEATURE:
<223> OTHER INFORMATION: AON hATXN3Ex9_1

<400> SEQUENCE: 144
gagauauguu ucuggaacua cc 22

<210> SEQ ID NO 145
<211> LENGTH: 21
<212> TYPE: DNA
<213> ORGANISM: Artificial
<220> FEATURE:
<223> OTHER INFORMATION: target hATXN3Ex9_2

<400> SEQUENCE: 145
gcttcggaag agacgagaag c 21

<210> SEQ ID NO 146
<211> LENGTH: 21
<212> TYPE: RNA
<213> ORGANISM: Artificial
<220> FEATURE:
<223> OTHER INFORMATION: AON hATXN3Ex9_2

<400> SEQUENCE: 146
gcuucucguc ucuuccgaag c 21

<210> SEQ ID NO 147
<211> LENGTH: 22
<212> TYPE: DNA
<213> ORGANISM: Artificial
<220> FEATURE:
<223> OTHER INFORMATION: target hATXN3Ex10_1

<400> SEQUENCE: 147
cagcagcaaa agcagcaaca gc 22

<210> SEQ ID NO 148
<211> LENGTH: 22
<212> TYPE: RNA
<213> ORGANISM: Artificial
<220> FEATURE:
<223> OTHER INFORMATION: AON hATXN3Ex10_1

<400> SEQUENCE: 148
gcuguugcug cuuuugcugc ug 22

<210> SEQ ID NO 149
<211> LENGTH: 20
<212> TYPE: DNA
<213> ORGANISM: Artificial
<220> FEATURE:
<223> OTHER INFORMATION: target hATXN3Ex10_2

<400> SEQUENCE: 149
gacctatcag gacagagttc 20

<210> SEQ ID NO 150
<211> LENGTH: 20
<212> TYPE: RNA
<213> ORGANISM: Artificial
<220> FEATURE:
<223> OTHER INFORMATION: AON hATXN3Ex10_2

<400> SEQUENCE: 150
gaacucuguc cugauagguc 20

<210> SEQ ID NO 151
<211> LENGTH: 21
<212> TYPE: DNA
<213> ORGANISM: Artificial
<220> FEATURE:
<223> OTHER INFORMATION: target hATXN7Ex3_1

<400> SEQUENCE: 151
gagcggaaag aatgtcggag c 21

<210> SEQ ID NO 152
<211> LENGTH: 21
<212> TYPE: RNA
<213> ORGANISM: Artificial
<220> FEATURE:
<223> OTHER INFORMATION: AON hATXN7Ex3_1

<400> SEQUENCE: 152
gcuccgacau ucuuuccgcu c 21

<210> SEQ ID NO 153

<211> LENGTH: 21
<212> TYPE: DNA
<213> ORGANISM: Artificial
<220> FEATURE:
<223> OTHER INFORMATION: target hATXN7Ex3_2

<400> SEQUENCE: 153
agcgggccgc ggatgacgtc a 21

<210> SEQ ID NO 154
<211> LENGTH: 21
<212> TYPE: RNA
<213> ORGANISM: Artificial
<220> FEATURE:
<223> OTHER INFORMATION: AON hATXN7Ex3_2

<400> SEQUENCE: 154
ugacgucauc cgcggcccgc u 21

<210> SEQ ID NO 155
<211> LENGTH: 20
<212> TYPE: DNA
<213> ORGANISM: Artificial
<220> FEATURE:
<223> OTHER INFORMATION: target hATXN7Ex3_3

<400> SEQUENCE: 155
agcagccgcc gcctccgcag 20

<210> SEQ ID NO 156
<211> LENGTH: 20
<212> TYPE: RNA
<213> ORGANISM: Artificial
<220> FEATURE:
<223> OTHER INFORMATION: AON hATXN7Ex3_3

<400> SEQUENCE: 156
cugcggaggc ggcggcugcu 20

<210> SEQ ID NO 157
<211> LENGTH: 19
<212> TYPE: DNA
<213> ORGANISM: Artificial
<220> FEATURE:
<223> OTHER INFORMATION: target hATXN7Ex3_4

<400> SEQUENCE: 157
acacggccgg aggacggcg 19

<210> SEQ ID NO 158
<211> LENGTH: 19
<212> TYPE: RNA
<213> ORGANISM: Artificial
<220> FEATURE:
<223> OTHER INFORMATION: AON hATXN7Ex3_4

<400> SEQUENCE: 158
cgccguccuc cggccgugu 19

<210> SEQ ID NO 159
<211> LENGTH: 21
<212> TYPE: DNA
<213> ORGANISM: Artificial
<220> FEATURE:
<223> OTHER INFORMATION: target hATXN7Ex3_5

<400> SEQUENCE: 159
gcgccgcctc cacctcggcc g 21

<210> SEQ ID NO 160
<211> LENGTH: 21
<212> TYPE: RNA
<213> ORGANISM: Artificial
<220> FEATURE:
<223> OTHER INFORMATION: AON hATXN7Ex3_5

<400> SEQUENCE: 160
cggccgaggu ggaggcggcg c 21

<210> SEQ ID NO 161
<211> LENGTH: 22
<212> TYPE: DNA
<213> ORGANISM: Artificial
<220> FEATURE:
<223> OTHER INFORMATION: target hATXN7Ex3_6

<400> SEQUENCE: 161
acctcggccg ccgcaatggc ga 22

<210> SEQ ID NO 162
<211> LENGTH: 22
<212> TYPE: RNA
<213> ORGANISM: Artificial
<220> FEATURE:
<223> OTHER INFORMATION: AON hATXN7Ex3_6

<400> SEQUENCE: 162
ucgccauugc ggcggccgag gu 22

<210> SEQ ID NO 163
<211> LENGTH: 22
<212> TYPE: DNA
<213> ORGANISM: Artificial
<220> FEATURE:
<223> OTHER INFORMATION: target hATXN7Ex3_7

<400> SEQUENCE: 163
ggcctctgcc cagtcctgaa gt 22

<210> SEQ ID NO 164
<211> LENGTH: 22
<212> TYPE: RNA
<213> ORGANISM: Artificial
<220> FEATURE:
<223> OTHER INFORMATION: AON hATXN7Ex3_7

<400> SEQUENCE: 164
acuucaggac ugggcagagg cc 22

<210> SEQ ID NO 165
<211> LENGTH: 23
<212> TYPE: DNA
<213> ORGANISM: Artificial
<220> FEATURE:
<223> OTHER INFORMATION: target hATXN7Ex3_8

<400> SEQUENCE: 165
tgatgctggg acagtcgtgg aat 23

<210> SEQ ID NO 166
<211> LENGTH: 23
<212> TYPE: RNA

<213> ORGANISM: Artificial
<220> FEATURE:
<223> OTHER INFORMATION: AON hATXN7Ex3_8

<400> SEQUENCE: 166
auuccacgac ugucccagca uca 23

<210> SEQ ID NO 167
<211> LENGTH: 23
<212> TYPE: DNA
<213> ORGANISM: Artificial
<220> FEATURE:
<223> OTHER INFORMATION: target hATXN7Ex3_9

<400> SEQUENCE: 167
aggcttccaa acttcctggg aag 23

<210> SEQ ID NO 168
<211> LENGTH: 23
<212> TYPE: RNA
<213> ORGANISM: Artificial
<220> FEATURE:
<223> OTHER INFORMATION: AON hATXN7Ex3_9

<400> SEQUENCE: 168
cuucccagga aguuuggaag ccu 23

<210> SEQ ID NO 169
<211> LENGTH: 29
<212> TYPE: DNA
<213> ORGANISM: Artificial
<220> FEATURE:
<223> OTHER INFORMATION: target hHTTEx12_1

<400> SEQUENCE: 169
catcagcgac agctcccaga ccaccaccg 29

<210> SEQ ID NO 170
<211> LENGTH: 29
<212> TYPE: RNA
<213> ORGANISM: Artificial
<220> FEATURE:
<223> OTHER INFORMATION: AON hHTTEx12_1

<400> SEQUENCE: 170 cgguggugg u cugggagcug ucgcugaug 29

<210> SEQ ID NO 171
<211> LENGTH: 20
<212> TYPE: DNA
<213> ORGANISM: Artificial
<220> FEATURE:
<223> OTHER INFORMATION: target hHTTEx12_2

<400> SEQUENCE: 171
tcacagcaca cactgcaggc 20

<210> SEQ ID NO 172
<211> LENGTH: 20
<212> TYPE: RNA
<213> ORGANISM: Artificial
<220> FEATURE:
<223> OTHER INFORMATION: AON hHTTEx12_2

<400> SEQUENCE: 172
gccugcagug ugugcuguga 20

<210> SEQ ID NO 173
<211> LENGTH: 22
<212> TYPE: DNA
<213> ORGANISM: Artificial
<220> FEATURE:
<223> OTHER INFORMATION: target hHTTEx12_3

<400> SEQUENCE: 173
ggtcagcagg tcatgacatc at 22

<210> SEQ ID NO 174
<211> LENGTH: 22
<212> TYPE: RNA
<213> ORGANISM: Artificial
<220> FEATURE:
<223> OTHER INFORMATION: AON hHTTEx12_3

<400> SEQUENCE: 174
augaugucau gaccugcuga cc 22

<210> SEQ ID NO 175
<211> LENGTH: 20
<212> TYPE: DNA
<213> ORGANISM: Artificial
<220> FEATURE:
<223> OTHER INFORMATION: target hHTTEx12_4

<400> SEQUENCE: 175
agagctggct gcttcttcag 20

<210> SEQ ID NO 176
<211> LENGTH: 20
<212> TYPE: RNA
<213> ORGANISM: Artificial
<220> FEATURE:
<223> OTHER INFORMATION: AON hHTTEx12_4

<400> SEQUENCE: 176
cugaagaagc agccagcucu 20

<210> SEQ ID NO 177
<211> LENGTH: 20
<212> TYPE: DNA
<213> ORGANISM: Artificial
<220> FEATURE:
<223> OTHER INFORMATION: target hHTTEx12_5

<400> SEQUENCE: 177
gatgaggagg atatcttgag 20

<210> SEQ ID NO 178
<211> LENGTH: 20
<212> TYPE: RNA
<213> ORGANISM: Artificial
<220> FEATURE:
<223> OTHER INFORMATION: AON hHTTEx12_5

<400> SEQUENCE: 178
cucaagauau ccuccucauc 20

<210> SEQ ID NO 179
<211> LENGTH: 23
<212> TYPE: DNA
<213> ORGANISM: Artificial
<220> FEATURE:

<223> OTHER INFORMATION: target hHTTEx12_6

<400> SEQUENCE: 179
tcagtgaagg atgagatcag tgg 23

<210> SEQ ID NO 180
<211> LENGTH: 23
<212> TYPE: RNA
<213> ORGANISM: Artificial
<220> FEATURE:
<223> OTHER INFORMATION: AON hHTTEx12_6

<400> SEQUENCE: 180
ccacugaucu cauccuucac uga 23

<210> SEQ ID NO 181
<211> LENGTH: 20
<212> TYPE: DNA
<213> ORGANISM: Artificial
<220> FEATURE:
<223> OTHER INFORMATION: target hHTTEx12_7

<400> SEQUENCE: 181
atggacctga atgatgggac 20

<210> SEQ ID NO 182
<211> LENGTH: 20
<212> TYPE: RNA
<213> ORGANISM: Artificial
<220> FEATURE:
<223> OTHER INFORMATION: AON hHTTEx12_7

<400> SEQUENCE: 182
gucccaucau ucagguccau 20

<210> SEQ ID NO 183
<211> LENGTH: 20
<212> TYPE: DNA
<213> ORGANISM: Artificial
<220> FEATURE:
<223> OTHER INFORMATION: target hHTTEx12_8

<400> SEQUENCE: 183
tgacaagctc tgccactgat 20

<210> SEQ ID NO 184
<211> LENGTH: 20
<212> TYPE: RNA
<213> ORGANISM: Artificial
<220> FEATURE:
<223> OTHER INFORMATION: AON hHTTEx12_8

<400> SEQUENCE: 184
aucaguggca gagcuuguca 20

<210> SEQ ID NO 185
<211> LENGTH: 20
<212> TYPE: DNA
<213> ORGANISM: Artificial
<220> FEATURE:
<223> OTHER INFORMATION: target hHTTEx12_9

<400> SEQUENCE: 185
tccagccagg tcagcgccgt 20

<210> SEQ ID NO 186
<211> LENGTH: 20
<212> TYPE: RNA
<213> ORGANISM: Artificial
<220> FEATURE:
<223> OTHER INFORMATION: AON hHTTEx12_9

<400> SEQUENCE: 186
acggcgcuga ccuggcugga 20

<210> SEQ ID NO 187
<211> LENGTH: 21
<212> TYPE: DNA
<213> ORGANISM: Artificial
<220> FEATURE:
<223> OTHER INFORMATION: target hHTTEx12_10

<400> SEQUENCE: 187
actcagtgga tctggccagc t 21

<210> SEQ ID NO 188
<211> LENGTH: 21
<212> TYPE: RNA
<213> ORGANISM: Artificial
<220> FEATURE:
<223> OTHER INFORMATION: AON hHTTEx12_10

<400> SEQUENCE: 188
agcuggccag auccacugag u 21

<210> SEQ ID NO 189
<211> LENGTH: 18
<212> TYPE: DNA
<213> ORGANISM: Artificial
<220> FEATURE:
<223> OTHER INFORMATION: target hHTTEx13_1

<400> SEQUENCE: 189
cctgcagatt ggacagcc 18

<210> SEQ ID NO 190
<211> LENGTH: 18
<212> TYPE: RNA
<213> ORGANISM: Artificial
<220> FEATURE:
<223> OTHER INFORMATION: AON hHTTEx13_1

<400> SEQUENCE: 190
ggcuguccaa ucugcagg 18

<210> SEQ ID NO 191
<211> LENGTH: 20
<212> TYPE: DNA
<213> ORGANISM: Artificial
<220> FEATURE:
<223> OTHER INFORMATION: target hHTTEx13_2

<400> SEQUENCE: 191
ggtaccgaca accagtattt 20

<210> SEQ ID NO 192
<211> LENGTH: 20
<212> TYPE: RNA
<213> ORGANISM: Artificial
<220> FEATURE:
<223> OTHER INFORMATION: AON hHTTEx13_2

<400> SEQUENCE: 192
aaauacuggu ugucgguacc 20

<210> SEQ ID NO 193
<211> LENGTH: 21
<212> TYPE: DNA
<213> ORGANISM: Artificial
<220> FEATURE:
<223> OTHER INFORMATION: target hHTTEx14_1

<400> SEQUENCE: 193
aacatgagtc actgcaggca g 21

<210> SEQ ID NO 194
<211> LENGTH: 21
<212> TYPE: RNA
<213> ORGANISM: Artificial
<220> FEATURE:
<223> OTHER INFORMATION: AON hHTTEx14_1

<400> SEQUENCE: 194
cugccugcag ugacucaugu u 21

<210> SEQ ID NO 195
<211> LENGTH: 22
<212> TYPE: DNA
<213> ORGANISM: Artificial
<220> FEATURE:
<223> OTHER INFORMATION: target hHTTEx14_2

<400> SEQUENCE: 195
gccttctgac agcagtgttg at 22

<210> SEQ ID NO 196
<211> LENGTH: 22
<212> TYPE: RNA
<213> ORGANISM: Artificial
<220> FEATURE:
<223> OTHER INFORMATION: AON hHTTEx14_2

<400> SEQUENCE: 196
aucaacacug cugucagaag gc 22

<210> SEQ ID NO 197
<211> LENGTH: 20
<212> TYPE: DNA
<213> ORGANISM: Artificial
<220> FEATURE:
<223> OTHER INFORMATION: target hHTTEx14_3

<400> SEQUENCE: 197
gttgagagat gaagctactg 20

<210> SEQ ID NO 198
<211> LENGTH: 20
<212> TYPE: RNA
<213> ORGANISM: Artificial
<220> FEATURE:
<223> OTHER INFORMATION: AON hHTTEx14_3

<400> SEQUENCE: 198
caguagcuuc aucucucaac 20

<210> SEQ ID NO 199
<211> LENGTH: 22

<212> TYPE: DNA
<213> ORGANISM: Artificial
<220> FEATURE:
<223> OTHER INFORMATION: target hTBPEx3_1:

<400> SEQUENCE: 199
gccatgactc ccggaatccc ta 22

<210> SEQ ID NO 200
<211> LENGTH: 22
<212> TYPE: RNA
<213> ORGANISM: Artificial
<220> FEATURE:
<223> OTHER INFORMATION: AON hTBPEx3_1:

<400> SEQUENCE: 200
uagggauucc gggagucaug gc 22

<210> SEQ ID NO 201
<211> LENGTH: 22
<212> TYPE: DNA
<213> ORGANISM: Artificial
<220> FEATURE:
<223> OTHER INFORMATION: target hTBPEx3_2:

<400> SEQUENCE: 201
cctatcttta gtccaatgat gc 22

<210> SEQ ID NO 202
<211> LENGTH: 22
<212> TYPE: RNA
<213> ORGANISM: Artificial
<220> FEATURE:
<223> OTHER INFORMATION: AON hTBPEx3_2:

<400> SEQUENCE: 202
gcaucauugg acuaaagaua gg 22

<210> SEQ ID NO 203
<211> LENGTH: 22
<212> TYPE: DNA
<213> ORGANISM: Artificial
<220> FEATURE:
<223> OTHER INFORMATION: target hTBPEx3_3:

<400> SEQUENCE: 203
tatggcactg gactgacccc ac 22

<210> SEQ ID NO 204
<211> LENGTH: 22
<212> TYPE: RNA
<213> ORGANISM: Artificial
<220> FEATURE:
<223> OTHER INFORMATION: AON hTBPEx3_3:

<400> SEQUENCE: 204
guggggucag uccagugcca ua 22

<210> SEQ ID NO 205
<211> LENGTH: 21
<212> TYPE: DNA
<213> ORGANISM: Artificial
<220> FEATURE:
<223> OTHER INFORMATION: target hTBPEx3_4:

<400> SEQUENCE: 205
gcagctgcag ccgttcagca g 21

<210> SEQ ID NO 206
<211> LENGTH: 21
<212> TYPE: RNA
<213> ORGANISM: Artificial
<220> FEATURE:
<223> OTHER INFORMATION: AON hTBPEx3_4:

<400> SEQUENCE: 206
cugcugaacg gcugcagcug c 21

<210> SEQ ID NO 207
<211> LENGTH: 22
<212> TYPE: DNA
<213> ORGANISM: Artificial
<220> FEATURE:
<223> OTHER INFORMATION: target hTBPEx3_5:

<400> SEQUENCE: 207
gttcagcagt caacgtccca gc 22

<210> SEQ ID NO 208
<211> LENGTH: 22
<212> TYPE: RNA
<213> ORGANISM: Artificial
<220> FEATURE:
<223> OTHER INFORMATION: AON hTBPEx3_5:

<400> SEQUENCE: 208
gcugggacgu ugacugcuga ac 22

<210> SEQ ID NO 209
<211> LENGTH: 22
<212> TYPE: DNA
<213> ORGANISM: Artificial
<220> FEATURE:
<223> OTHER INFORMATION: target hTBPEx3_6:

<400> SEQUENCE: 209
aacctcaggc caggcaccac ag 22

<210> SEQ ID NO 210
<211> LENGTH: 22
<212> TYPE: RNA
<213> ORGANISM: Artificial
<220> FEATURE:
<223> OTHER INFORMATION: AON hTBPEx3_6:

<400> SEQUENCE: 210
cuguggugcc uggccugagg uu 22

<210> SEQ ID NO 211
<211> LENGTH: 21
<212> TYPE: DNA
<213> ORGANISM: Artificial
<220> FEATURE:
<223> OTHER INFORMATION: target hTBPEx3_7:

<400> SEQUENCE: 211
gcaccacagc tcttccactc a 21

<210> SEQ ID NO 212
<211> LENGTH: 21
<212> TYPE: RNA
<213> ORGANISM: Artificial

<220> FEATURE:
<223> OTHER INFORMATION: AON hTBPEx3_7:

<400> SEQUENCE: 212
ugaguggaag agcuguggug c 21

<210> SEQ ID NO 213
<211> LENGTH: 21
<212> TYPE: DNA
<213> ORGANISM: Artificial
<220> FEATURE:
<223> OTHER INFORMATION: target hTBPEx3_8:

<400> SEQUENCE: 213
ctcacagact ctcacaactg c 21

<210> SEQ ID NO 214
<211> LENGTH: 21
<212> TYPE: RNA
<213> ORGANISM: Artificial
<220> FEATURE:
<223> OTHER INFORMATION: AON hTBPEx3_8:

<400> SEQUENCE: 214
gcaguuguga gagucuguga g 21

<210> SEQ ID NO 215
<211> LENGTH: 22
<212> TYPE: DNA
<213> ORGANISM: Artificial
<220> FEATURE:
<223> OTHER INFORMATION: target hTBPEx3_9:

<400> SEQUENCE: 215
ggcaccactc cactgtatcc ct 22

<210> SEQ ID NO 216
<211> LENGTH: 22
<212> TYPE: RNA
<213> ORGANISM: Artificial
<220> FEATURE:
<223> OTHER INFORMATION: AON hTBPEx3_9:

<400> SEQUENCE: 216
agggauacag uggaguggug cc 22

<210> SEQ ID NO 217
<211> LENGTH: 22
<212> TYPE: DNA
<213> ORGANISM: Artificial
<220> FEATURE:
<223> OTHER INFORMATION: target hTBPEx3_10:

<400> SEQUENCE: 217
catcactcct gccacgccag ct 22

<210> SEQ ID NO 218
<211> LENGTH: 22
<212> TYPE: RNA
<213> ORGANISM: Artificial
<220> FEATURE:
<223> OTHER INFORMATION: AON hTBPEx3_10:

<400> SEQUENCE: 218
agcuggcgug gcaggaguga ug 22

<210> SEQ ID NO 219
<211> LENGTH: 22
<212> TYPE: DNA
<213> ORGANISM: Artificial
<220> FEATURE:
<223> OTHER INFORMATION: target hTBPEx3_11:

<400> SEQUENCE: 219
agagttctgg gattgtaccg ca 22

<210> SEQ ID NO 220
<211> LENGTH: 22
<212> TYPE: RNA
<213> ORGANISM: Artificial
<220> FEATURE:
<223> OTHER INFORMATION: AON hTBPEx3_11:

<400> SEQUENCE: 220
ugcgguacaa ucccagaacu cu 22

<210> SEQ ID NO 221
<211> LENGTH: 22
<212> TYPE: DNA
<213> ORGANISM: Artificial
<220> FEATURE:
<223> OTHER INFORMATION: target hTBPEx4_1:

<400> SEQUENCE: 221
tgtatccaca gtgaatcttg gt 22

<210> SEQ ID NO 222
<211> LENGTH: 22
<212> TYPE: RNA
<213> ORGANISM: Artificial
<220> FEATURE:
<223> OTHER INFORMATION: AON hTBPEx4_1:

<400> SEQUENCE: 222
accaagauuc acuguggaua ca 22

<210> SEQ ID NO 223
<211> LENGTH: 21
<212> TYPE: DNA
<213> ORGANISM: Artificial
<220> FEATURE:
<223> OTHER INFORMATION: target hTBPEx4_2:

<400> SEQUENCE: 223
ggttgtaaac ttgacctaaa g 21

<210> SEQ ID NO 224
<211> LENGTH: 21
<212> TYPE: RNA
<213> ORGANISM: Artificial
<220> FEATURE:
<223> OTHER INFORMATION: AON hTBPEx4_2:

<400> SEQUENCE: 224
cuuuagguca aguuuacaac c 21

<210> SEQ ID NO 225
<211> LENGTH: 23
<212> TYPE: DNA
<213> ORGANISM: Artificial
<220> FEATURE:
<223> OTHER INFORMATION: target hTBPEx4_3:

<400> SEQUENCE: 225
cattgcactt cgtgcccgaa acg 23

<210> SEQ ID NO 226
<211> LENGTH: 23
<212> TYPE: RNA
<213> ORGANISM: Artificial
<220> FEATURE:
<223> OTHER INFORMATION: AON hTBPEx4_3:

<400> SEQUENCE: 226
cguuucgggc acgaagugca aug 23

<210> SEQ ID NO 227
<211> LENGTH: 240
<212> TYPE: PRT
<213> ORGANISM: Homo sapiens

<400> SEQUENCE: 227

Ser Ile Val Glu Leu Ile Ala Gly Gly Gly Ser Ser Cys Ser Pro Val
1 5 10 15

Leu Ser Arg Lys Gln Lys Gly Lys Val Leu Leu Gly Glu Glu Glu Ala
20 25 30

Leu Glu Asp Asp Ser Glu Ser Arg Ser Asp Val Ser Ser Ser Ala Leu
35 40 45

Thr Ala Ser Val Lys Asp Glu Ile Ser Gly Glu Leu Ala Ala Ser Ser
50 55 60

Gly Val Ser Thr Pro Gly Ser Ala Gly His Asp Ile Ile Thr Glu Gln
65 70 75 80

Pro Arg Ser Gln His Thr Leu Gln Ala Asp Ser Val Asp Leu Ala Ser
85 90 95

Cys Asp Leu Thr Ser Ser Ala Thr Asp Gly Asp Glu Glu Asp Ile Leu
100 105 110

Ser His Ser Ser Ser Gln Val Ser Ala Val Pro Ser Asp Pro Ala Met
115 120 125

Asp Leu Asn Asp Gly Thr Gln Ala Ser Ser Pro Ile Ser Asp Ser Ser
130 135 140

Gln Thr Thr Thr Glu Gly Pro Asp Ser Ala Val Thr Pro Ser Asp Ser
145 150 155 160

Ser Glu Ile Val Leu Asp Gly Thr Asp Asn Gln Tyr Leu Gly Leu Gln
165 170 175

Ile Gly Gln Pro Gln Asp Glu Asp Glu Glu Ala Thr Gly Ile Leu Pro
180 185 190

Asp Glu Ala Ser Glu Ala Phe Arg Asn Ser Ser Met Ala Leu Gln Gln
195 200 205

Ala His Leu Leu Lys Asn Met Ser His Cys Arg Gln Pro Ser Asp Ser
210 215 220

Ser Val Asp Lys Phe Val Leu Arg Asp Glu Ala Thr Glu Pro Gly Asp
225 230 235 240

<210> SEQ ID NO 228
<211> LENGTH: 16
<212> TYPE: DNA
<213> ORGANISM: Homo sapiens

<400> SEQUENCE: 228
cagccaggtc agcgcc 16

```
<210> SEQ ID NO 229
<211> LENGTH: 16
<212> TYPE: DNA
<213> ORGANISM: Artificial
<220> FEATURE:
<223> OTHER INFORMATION: skipped PCR product of HDEx12_1

<400> SEQUENCE: 229

cagccaggtg ttagac                                                       16


<210> SEQ ID NO 230
<211> LENGTH: 172
<212> TYPE: PRT
<213> ORGANISM: Homo sapiens
<220> FEATURE:
<221> NAME/KEY: DOMAIN
<222> LOCATION: (49)..(52)
<223> OTHER INFORMATION: caspase cleavage motif
<220> FEATURE:
<221> NAME/KEY: DOMAIN
<222> LOCATION: (88)..(91)
<223> OTHER INFORMATION: caspase cleavage motif
<220> FEATURE:
<221> NAME/KEY: DOMAIN
<222> LOCATION: (122)..(125)
<223> OTHER INFORMATION: caspase cleavage motif

<400> SEQUENCE: 230

Asp Val Ser Ser Ser Ala Leu Thr Ala Ser Val Lys Asp Glu Ile Ser
1               5                   10                  15

Gly Glu Leu Ala Ala Ser Ser Gly Val Ser Thr Pro Gly Ser Ala Gly
            20                  25                  30

His Asp Ile Ile Thr Glu Gln Pro Arg Ser Gln His Thr Leu Gln Ala
        35                  40                  45

Asp Ser Val Asp Leu Ala Ser Cys Asp Leu Thr Ser Ser Ala Thr Asp
    50                  55                  60

Gly Asp Glu Glu Asp Ile Leu Ser His Ser Ser Ser Gln Val Ser Ala
65                  70                  75                  80

Val Pro Ser Asp Pro Ala Met Asp Leu Asn Asp Gly Thr Gln Ala Ser
                85                  90                  95

Ser Pro Ile Ser Asp Ser Ser Gln Thr Thr Thr Glu Gly Pro Asp Ser
            100                 105                 110

Ala Val Thr Pro Ser Asp Ser Ser Glu Ile Val Leu Asp Gly Thr Asp
        115                 120                 125

Asn Gln Tyr Leu Gly Leu Gln Ile Gly Gln Pro Gln Asp Glu Asp Glu
    130                 135                 140

Glu Ala Thr Gly Ile Leu Pro Asp Glu Ala Ser Glu Ala Phe Arg Asn
145                 150                 155                 160

Ser Ser Met Ala Leu Gln Gln Ala His Leu Leu Lys
                165                 170


<210> SEQ ID NO 231
<211> LENGTH: 78
<212> TYPE: DNA
<213> ORGANISM: Homo sapiens
<220> FEATURE:
<221> NAME/KEY: CDS
<222> LOCATION: (1)..(78)

<400> SEQUENCE: 231

tcc agc cag gtc agc gcc gtc cca tct gac cct gcc atg gac ctg aat         48
Ser Ser Gln Val Ser Ala Val Pro Ser Asp Pro Ala Met Asp Leu Asn
```

```
1               5                   10                  15

gat ggg acc cag gcc tcg tcg ccc atc agc                              78
Asp Gly Thr Gln Ala Ser Ser Pro Ile Ser
            20                  25



<210> SEQ ID NO 232
<211> LENGTH: 26
<212> TYPE: PRT
<213> ORGANISM: Homo sapiens


<400> SEQUENCE: 232

Ser Ser Gln Val Ser Ala Val Pro Ser Asp Pro Ala Met Asp Leu Asn
1               5                   10                  15

Asp Gly Thr Gln Ala Ser Ser Pro Ile Ser
            20                  25


<210> SEQ ID NO 233
<211> LENGTH: 78
<212> TYPE: DNA
<213> ORGANISM: Homo sapiens
<220> FEATURE:
<221> NAME/KEY: CDS
<222> LOCATION: (1)..(78)


<400> SEQUENCE: 233

gac agc tcc cag acc acc acc gaa ggg cct gat tca gct gtt acc cct      48
Asp Ser Ser Gln Thr Thr Thr Glu Gly Pro Asp Ser Ala Val Thr Pro
1               5                   10                  15

tca gac agt tct gaa att gtg tta gac ggt                              78
Ser Asp Ser Ser Glu Ile Val Leu Asp Gly
            20                  25


<210> SEQ ID NO 234
<211> LENGTH: 26
<212> TYPE: PRT
<213> ORGANISM: Homo sapiens

<400> SEQUENCE: 234

Asp Ser Ser Gln Thr Thr Thr Glu Gly Pro Asp Ser Ala Val Thr Pro
1               5                   10                  15

Ser Asp Ser Ser Glu Ile Val Leu Asp Gly
            20                  25
```